US005817823A

United States Patent [19]
Hong et al.

[11] Patent Number: 5,817,823
[45] Date of Patent: Oct. 6, 1998

[54] METHOD FOR SYNTHESIZING 2-SUBSTITUTED IMIDAZOLES

[75] Inventors: Yaping Hong, Framingham; Roger P. Bakale; Chrisantha H. Senanayake, both of Shrewsbury, all of Mass.

[73] Assignee: Sepracor Inc., Marlborough, Mass.

[21] Appl. No.: 840,910

[22] Filed: Apr. 17, 1997

[51] Int. Cl.$^6$ ............ C07D 401/00; C07D 401/04; C07D 401/12; C07D 401/14
[52] U.S. Cl. ............ 546/199; 548/306.4; 548/309.4; 548/310.4; 548/331.5; 546/210
[58] Field of Search ............ 546/199; 548/331.5

[56] References Cited

U.S. PATENT DOCUMENTS

| | | | |
|---|---|---|---|
| 3,798,232 | 3/1974 | Wittekind et al. | 546/210 X |
| 3,840,554 | 10/1974 | Wittekind et al. | 546/210 X |
| 3,976,778 | 8/1976 | Nagarajan et al. | 546/210 X |
| 4,219,559 | 8/1980 | Janssens et al. | 424/267 |
| 4,588,722 | 5/1986 | Janssens et al. | 514/228 |
| 4,634,704 | 1/1987 | Janssens et al. | 514/253 |
| 4,835,161 | 5/1989 | Janssens et al. | 514/303 |
| 5,380,858 | 1/1995 | Durant et al. | 546/278 |

FOREIGN PATENT DOCUMENTS

| | | |
|---|---|---|
| 1327579 | 3/1994 | Canada . |
| 0 055 099 | 6/1982 | European Pat. Off. . |
| 0 055 562 | 7/1982 | European Pat. Off. . |
| 0 082 648 | 6/1983 | European Pat. Off. . |
| 0 099 139 | 1/1984 | European Pat. Off. . |
| 0 145 037 | 6/1985 | European Pat. Off. . |
| 0 151 824 | 8/1985 | European Pat. Off. . |
| 0 232 937 | 8/1987 | European Pat. Off. . |
| 2 317 453 | 10/1973 | Germany . |
| 4041173 | 6/1992 | Germany . |
| 4294681 | 7/1993 | Germany . |
| 4232524 | 3/1994 | Germany . |
| 62-215575 | 9/1987 | Japan . |
| 7-179458 | 7/1995 | Japan . |
| 1230393 | 4/1971 | United Kingdom . |
| 2267287 | 12/1993 | United Kingdom . |

OTHER PUBLICATIONS

Balli and Maul, 1976, "Azidinium Salts. Part 17. Azidinium Salts and Triazatrimethinecyanines of Substituted Benzimidazoles", Helv. Chim. Acta 59:148–155 (in German with English abstract).

Balli and Kersting, 1961, "Azidiniumsalze, I. Synthese Quasiaromatischer Azidocyclimonium–Fluoroborate", Annalen der Chemie 647:1–10 (in German).

Barrio et al., 1996, "Elemental Fluorine to 8–Fluoropurines in One Step", J. Am. Chem Soc. 118:10408–10411.

Clark et al., 1986, "Calcium Fluoride–Supported Alkalai Metal Fluorides. New Reagents for Nucleophilic Fluorine Transfer Reactions", J. Chem. Soc. Chem. Commun. pp. 791–793.

Coad et al., 1996, "Synthesis, Characterization, and Thermolysis of $C_{15}N_{12}$", J. Org. Chem. 61:6666–6672.

Coad and Rasmussen, 1995, "Synthesis and Characterization of Novel Carbon–Nitrogen Materials by Thermolysis of Monomers and Dimers of 4,5–Dicyanoimidazole", Am. Chem. Soc. Symp. Ser., Fire and Polymers II, pp. 256–266.

El Borai et al., 1981, "Synthesis of Halogen Derivatives of N–Methylimidazole", Polish J. Chem. 55:1659–1665.

Eltsov et al., 1970, Zh. Org. Khim. 6:635–636 (in Russian).

Glowczyk and Serafin, 1984, "Reaction of 2–Substituted Benzimidazolium Derivatives with Nucleophilic Agents. Part I." Polish J. Chem. 58:149–156.

Grabowski et al., 1974, "An Efficient and Selective Method for the Synthesis of 2–(4–Fluorophenyl)–1–(2–Hydroxyethyl)–5–Nitroimidazole (Flunidazole)", J. Med. Chem. 17:547–549.

Grimmett, 1984, "Imidazoles and their Benzo Derivatives: (ii) Reactivity; (iii) Synthesis and Applications" in: Comprehensive Heterocyclic Chemistry, vol. 5, pp. 373–498, A.R. Katritsky, ed., Pergamon Press, Oxford.

Ichihara et al., 1986, "The Combination of Potassium Fluoride and Calcium Fluoride: A Useful Heterogeneous Fluorinating Reagent", J. Chem. Soc. Chem. Commun. 793–794.

Janssens et al., 1985, "New Antihistaminic N–Heterocyclic 4–Piperidinamines. 1. Synthesis and Antihistaminic Activity of N–(4–Piperidinyl)–1H–Benzimidazol–2–amines", J. Med. Chem. 28:1925–1933.

Janssens et al., 1985, "New Antihistaminic N–Heterocyclic 4–Piperidinamines. 2. Synthesis and Antihistaminic Activity of 1–[(4–Fluorophenyl)methyl]–N–(4–piperidinyl)–1H–Benzimidazol–2–amines", J. Med. Chem. 28:1934–1943.

Janssens et al., 1985, "New Antihistaminic N–Heterocyclic 4–Piperidinamines. 3. Synthesis and Antihistaminic Activity of N–(4–piperidenyl)–3H–imidazo–[4,5b]pyridin–2–amines", J. Med. Chem. 28:1943–1947.

Joule, 1995, "1,3–Azoles: Imidazoles, Thiazoles and Oxazoles. 21.8 Electrocyclic and Photochemical Reactions", Heterocycle Chemistry, 3rd. ed., pp. 378–380, Chapman and Hall, London.

Jung et al., 1993, "Synthesis and Structure–Activity Relationships of New Cephalosporins with Aminoimidazoles at C–7; Effect of the pKa of the C–7 Aminoimidazole on Antibacterial Spectrum and β–Lactamase Stability", J. Antibiotics 46:992–1012.

(List continued on next page.)

Primary Examiner—Floyd D. Higel
Attorney, Agent, or Firm—Pennie & Edmonds LLP

[57] ABSTRACT

The present invention is a method of preparing 2-substituted imidazoles from readily available imidazoles having a leaving group in the 2-position, by alkylating the imidazole under mild conditions to afford a 3-N-alkylated imidazolium salt; and coupling the imidazolium salt with a nucleophile also under mild conditions to afford a 2-substituted 3-N-alkylated imidazolium salt. The reaction product can optionally be isolated and purified. The 2-substituted 3-N-alkylated imidazolium salt is hydrolyzed to afford a 2-substituted imidazole. Alternatively, the imidazole is coupled with a nucleophile in the presence of fluoride ion to provide a 2-substituted imidazole.

57 Claims, No Drawings

OTHER PUBLICATIONS

Kochergin et al., 1993, "Investigation in the Imidazole Series. 94. Synthesis of Pyrrolo[1,2-a]benzimidazolyl-4-Acetic Acid Derivatives" Khim. Geterotsikl. Soedin. 5:659–663 (in russian with English abstract).

Kuzmenko et al., 1982, "Unusual Cleavage of Phenacyl-Substituted Benzimidazolium Salts. Synthesis of 1,4-Diarylimidazoles", Khim. Geterosikl. Soedin. 18:293–297 (translated from Russian).

Kuzmenko et al., 1982, "", Khim. Getrotsikl. Soedin. 18:388–392 (in Russian).

Macco et al., 1975, "2-(2-Imizazolyl)acetophenones. Preparation and Some Reactions" J. Org. Chem. 40:252–255.

Makovetskii et al., 1982, "Reaction of 2-Amino-3-(1-Methylbenzimidazol-2-yl)Benzo[b]furan with α-Halocarbonyl Compounds", Dopov. Akad. Nauk Ukr. RSR, Ser. B: Geol., Khim. Biol. Nauki 1:54–56 (in Russian with English abstract).

Marquez et al., 1990, "Acid-Stable 2'-Fluoro Purine Dideoxynucleosides as Active Agents Against HIV", J. Med. Chem. 33:978–985.

Matsuda et al., 1992, "Thermal Reaction of Benzimidazolium N-Allylides", Heterocycles 33:295–302.

Meth-Cohn, 1964, "Acylation of Benzimidazoles", J. Chem. Soc. No. 1004, p. 5245-5–5247.

Mushkalo and Turova, 1981, "Biscyanines with Nonconjugated Chromophores from N,N'-Polymethylenebis(benzimidazolium) Salts", Ukr. Khim. Zh. 47:519–522 (in Russian with English abstract).

McClelland et al., 1984, "2-Hydroxylaminoimidazoles—Unstable Intermediates in the Reduction of 2-Nitroimidazoles", Biochem. Pharmacol. 33:303–309.

Naik et al., 1973, "A Novel Route to 3(5)-Fluoro-1,2,4-triazoles and 8-Fluoropurines by Displacement of the Nitro Group", J. Org. Chem. 38:4353–4354.

Ott et al., 1956, "Oxazole Quaternary Salts", J. Am. Chem. Soc. 78:1941–1944.

Pernak et al., 1993, "3-Alkoxymethyl-1-ethyl-, 3-Alkylthiomethyl-1-ethyl, 3-Alkoxymethyl-1-butyl-und 3-Alkylthiomethyl-1-butylbenzimidazolium-chloride", Arch. Pharm. 326:237–240 (in German with English Abstract).

Pozharskii et al., 1966, "Advances in the Chemistry of Imidazole" Russian Chem. Rev. 35:122–144.

Preston, 1974, "Synthesis, Reactions, and Spectroscopic Properties of Benzimidazoles", Chem. Rev. 74:279–314.

Ricci et al., 1969, "Sintesi e Reagibilita di Alcuni Perclorati del 2-chloro-N,N'-dimetil-benzimidazolo-5(6)-X-sostituito", Bollettino 27:153–156 (in Italian).

Ruggli et al., 1929, "Uber Benzoylderivate des Diamino-Athylens und ihre Umwandlung in Imidazolone. I. Mitteilung uber Imidazol-Spaltungsproduckte", Helv. Chim. Acta 12:332–366 (in German).

Sheppard and Webster, 1973, "Hydrogen Cyanide Chemistry. V. Diazodicyanoimidazole and Dicyanoimidazole Halonium Ylides", J. Am. Chem. Soc. 95:2695–2697.

Skulski and Wroczynski, 1982, "Some New Halo- and Cyano-Demercuration Reactions of 9-Acetoxymercuri- and 8,8'-Mercurbis-Caffeines", Polish J. Chem. 56:975–982.

Smith, 1981, "Benzimidazole N-Oxides", In: Benzimidazoles and Congeneric Tricyclic Compounds, Part 1, pp. 287–329, P. Preston, ed., John Wiley & Sons, New York.

Sono et al., 1996, "Functionalization Including Fluorination of Nitrogen-Containing Compounds Using Electrochemical Oxidation", Chem. Pharm. Bull. 44:1141–1145.

Subrayan and Rasmussen, 1995, "Syntheses and Characterization of Aromatic Secondary and Tertiary Amines and a New Imidazolone From Dicyanoimidazole", Tetrahedron 51:6167–6178.

Subrayan et al., 1994, "Synthesis and Properties of Bis- and Tris(4,5-dicyano-1-methyl-2-imidazolyl)amines: A New Acidic Secondary Amine and a Nonbasic Tertiary Amine", J. Org. Chem. 59:4341–4345.

Takahashi et al., 1973, "Studies on Heteroaromatic N-Oxides. XI. Aminolysis of Esters of Benzazole N-Oxides and Related Quaternary Salts", Chem. Pharm. Bull. 21:287–295.

Takahashi and Kano, 1966, "Benzimidazole N-Oxides. VI. Reaction of 3-Methoxy-1-methyl- and 1,2-Dimethylbenzimidazolium Iodide with Various Nucleophiles", Chem. Pharm. Bull. 14:375–385.

Takahashi and Kano, 1964, "Benzimidazole N-Oxides. II. The Reactivity of 1-Alkoxybenzimidazoles", Chem. Pharm. Bull. 12:282–291.

Takahashi and Kano, 1964, "Benzimidazole N-Oxides. IV. 1,3-Dipolar Cycloaddition Reaction with !-Methylbenzimidazole 3-Oxide", Chem. Pharm. Bull. 12:1290–1295.

Vilarrasa et al., 1975, "Synthesis of Fluoroazoles", An. Quim. 71:631–632 (in Spanish with English abstract).

Wolff et al., 1980, "Benzimidazoliumsalze durch Nucleophile Aromatische Substitution", Arch. Pharm. 313:266–279 (in German with English abstract).

METHOD FOR SYNTHESIZING 2-SUBSTITUTED IMIDAZOLES

1. FIELD OF THE INVENTION

This invention relates to novel methods for synthesizing 2-substituted imidazoles, including norastemizole.

2. BACKGROUND OF THE INVENTION

2-Substituted imidazoles, and in particular, 2-aminosubstituted benzimidazoles such as 1-((4-fluorophenyl)-methyl)-N-(4-piperidinyl)-1H-benzimidazol-2-amine ("norastemizole"), have been described as having anti-histaminic properties (U.S. Pat. No. 4,219,559 to F. Janssens et al.; U.S. Pat. No. 4,835,161 to Janssens et al.; F. Janssens et al., J. Med. Chem. 28:1925 (1985)). Imidazoles substituted at the 3-position with N-heterocyclyl-4-piperidineamines have been reported to have histamine- and serotonin-agonist activity (European Patent Publication 0 099 139 B1; European Patent Publication 0 145 037 B1). Accordingly, efficient methods for obtaining such compounds are desirable.

Of particular difficulty and accordingly, importance, has been the pursuit of an efficient means for introducing substitution at the 2-position of an imidazole. 2-Substituted imidazoles, and in particular norastemizole, have been prepared via a cyclodesulfurization reaction of a thiourea being substituted at one of the thiourea nitrogen atoms with a 2-anilino group (U.S. Pat. No. 4,219,559 to Janssens et al.). Such a reaction proceeds in the presence of a potent alkylating agent, e.g., iodomethane, or a heavy metal salt, e.g., a mercury or lead salt, and is therefore disfavored from a toxicological and environmental standpoint. Accordingly, alternate means of obtaining 2-substituted imidazoles, and in particular, norastemizole, are highly desirable.

Another approach to 2-substituted imidazoles has been to react a 2-halosubstituted imidazole with an amine. For example, 2-Fluoroimidazoles have been shown to react with various amines to form 2-amino-substituted imidazoles (E. C. Coad et al., *J. Org. Chem.* 61:6666–6672 (1996); R. P. Subrayan et al., *Tetrahedron* 51(22):6167–6178 (1995); E. C. Coad et al., *Synthesis and Characterization of Novel Carbon-Nitrogen Materials by Thermolysis of Monomers and Dimers* of 4,5-Dicyanoimidazole, in ACS Symp. Ser., 1995, 599 (Five and Polymers II), 256–66 (1995); R. P. Subrayan et al.,*J. Org. Chem.* 59:4341–4345 (1994); F. Jung et al., J. Antibiot. 46(6):992–1012 (1993); European Patent Publication No. 082 648 A2; European Patent Publication 055 562 A2; European Patent Publication 055 099 A1). A disadvantage associated with this approach, however, is that the 2-fluoroimidazole used in the amination reaction must be used in purified, isolated form. In addition, where the 2-fluoroimidazole does not bear electron withdrawing groups directly on the imidazole ring, acid catalysis is generally required to effect the reaction, which can interfere with any acid-labile functional groups that reside on either the imidazole nucleus or the amino group-bearing nucleophile, and result in low yields of product.

2-Chloro-1-methylbenzimidazole had been shown to react with methylamine to afford 1-methyl-2-methylaminobezimidazole (S. Takahashi et al., *Chem. Pharm. Bull.* 14(4):375–385 (1966)). However, forcing conditions which are unsuitable for many synthetic transformations were required for product formation (i.e., 120° C., 3 hours, sealed tube).

Norastemizole was reported to have been prepared by a method similar to that described above. 2-Chloro-1-(4-fluorophenylmethyl)-1H-benzimidazole was reacted with ethyl 4-amino-1-piperidinecarboxylate, and the ethoxycarbonyl protecting group of the resulting product was hydrolyzed to afford norastemizole (U.S. Pat. No. 4,835,161 to Janssens et al.). Like the above method, a major disadvantage to this approach is that the forcing reaction conditions (120° C., >43 hours) required to effect the displacement of the 2-chloro group of the benzimidazole with the reactive amino species, will likely lead to decomposition of imidazoles bearing sensitive functional groups, including those imidazoles useful as synthetic intermediates for sophisticated imidazole targets. Accordingly, improved means for obtaining 2-substituted imidazoles and in particular norastemizole, would be quite useful.

An approach to the synthesis of 2-substituted imidazoles has been to "activate" the imidazole moiety via conversion to its 3-N-substituted imidazolium salt. In this way, the 2-position of the 3-N-substituted imidazolium salt has enhanced reactivity toward nucleophiles. Several approaches used to obtain 3-N-substituted imidazolium species are described below.

2-Substituted benzimidazolium 3-N-oxides, unable to be obtained from peroxide oxidation from benzimidazoles, have been prepared via a cyclization of 2-aminoanilides, 1-nitrosoanilines, and 1-nitro-N-substituted anilines (D. M. Smith, *Benzimidazoles and Congeneric Tricyclic Compounds*, Part 2 in *The Chemistry of Heterocyclic Compounds*, P. N. Preston, ed., pp. 287–306, John Wiley & Sons, New York (1981); M. R. Crimmett, *Comprehensive Heterocyclic Chemistry*, Vol. 5, A. R. Katritsky, ed., pp. 373–498, Pergamon Press, Oxford (1984)). Such benzimidazolium 3-N-oxides can be O-alkylated (D. M. Smith, *Benzimidazoles and Congeneric Tricyclic Compounds*, Part 2 in *The Chemistry of Heterocyclic Compounds*, P. N. Preston, ed., pp. 287–306, John Wiley & Sons, New York (1981); M. R. Crimmett, *Comprehensive Heterocyclic Chemistry*, Vol. 5, A. R. Katritsky, ed., pp. 373–498, Pergamon Press, Oxford (1984)). O-Alkylated benzimidazolium 3-N-oxides that are unsubstituted in the 2-position can react at the 2-position thereof with a variety of nucleophiles to afford 2-substituted benzimidazoles (S. Takahashi, *Chem. Pharm. Bull.* 12(3):282–291 (1964); S. Takahashi, *Chem. Pharm. Bull.* 12(11):1290–1295 (1964); and S. Takahashi, *Chem. Pharm. Bull.* 14(4):375–385 (1966). However, a significant problem with this approach has been that the cyclization reactions used to prepare the benzimidazolium 3-N-oxide starting materials proceed in less than desirable yield when performed on a large scale (P. N. Preston, *Chem. Rev.* 74(3):279–314 (1974)).

Further, 3-N-acylimidazolium salts have been obtained from the treatment of imidazoles with acid chlorides (J. A. Joule et al., *Heterocycle Chemistry*, 3rd ed., pp. 379–381, Chapman and Hall, London (1995); A. Macco et al.,*J. Org. Chem.* 40:252 (1975); D. G. Ott et al., *J. Am. Chem. Soc.* 78:1941 (1956); P. Ruggli et al., *Helv. Chim. Acta.* 12:332 (1929); and O. J. Heth-Cohn, *J. Chem. Soc.* 5245 (1964)). However, 3-N-acylimidazolium salts are unstable and accordingly, have limited utility as synthetic intermediates for, inter alia, 2-substituted imidazoles.

3-N-Alkylimidazolium salts have been prepared via alkylation of 2-substituted imidazoles with alkyl halides, alkoxymethyl halides and alkylthiomethyl halides (J. Glowczyk et al., *Polish J. Chem.* 58:149–156 (1984); J. Pernak, *Arch. Pharm.* (Weinheim, Ger.) 326(4):237–40 (1993); P. M. Kochergin et al., *Khim. Geterotsikl. Soedin.* 5:659–663 (1993); T. A. Kuz'menko et al., *Khim. Geterotsikl. Soedin.* 3:388–392 (1982); Y. Matsuda et al.,

*Heterocycles* 33(1):295–302 (1992); V. P. Makovetskii et al., *Dopov. Akad. Nauk. Ukr. RSR, Ser. B: Khim. Biol. Nauk.* 1:54–57 (1982); I. L. Mushkalo et al., *Ukr. Khim. Zh.* (Russ. Ed.) 47(5):519–522 (1981); German Patent Publication DE 4 232 524 A1; A. Ricci et al., *Bollettino* 27:153–156 (1969)), as well as with alkyl sulfates (A. Ricci et al., *Bollettino* 27:153–156 (1969)), oxonium salts (H. von Balli et al., *Ann.* 647(1):1–10 (1961); H. von Balli et al., *Helv. Chim. Acta* 59:148–155 (1976); and S. Takahashi et al., *Chem. Pharm. Bull.* 21:287 (1973)) and oxazolines (German Patent Publication DE 4 041 173 A1; German Patent Publication 42 946 481 C2; A. V. El'tsov et al., *Zh. Org. Khim.* 6:635 (1970); H.-M. Wolff et al., *Arch. Pharm. (Weinheim)* 313:266–279 (1980); United Kingdom Patent Publication GB 2 267 287 A1; and United Kingdom Patent Publication GB 1 230 393). In addition, one particular 3-N-alkylimidazolium species, i.e., 1,3-N,N-diethyl-2-chloroimidazolium tetrafluoroborate, has been shown to react with sodium azide to afford 1,3-N,N-diethyl-2-azidoimidazolium tetrafluoroborate, presumably via an addition-elimination reaction (H. von Balli et al., *Ann.* 647(1):1–10 (1961); H. von Balli et al., *Helv. Chim. Acta* 59:148–155 (1976)). However, the use of 3-alkylimidazolium salts is limited, in most cases, as a starting material for products that are themselves 3-alkylimidazolium salts, since the 3-alkyl group can be difficult to remove from the 3-imidazolium nitrogen, especially if one seeks to preserve the integrity of other functionality which may be present on the imidazole ring.

3-N-Alkoxyimidazolium salts are also known. For example, 3-N-methoxy-1-N-methylbenzimidazolium iodide has been shown to react with methylamine to afford 1-methyl-2-methylaminobezimidazole in approximately 20% yield (S. Takahashi et al., *Chem. Pharm. Bull.* 14(4):375–385 (1966)). While this reaction was reported to proceed under relatively mild conditions (i.e., 20°–25° C. for 1 hour), the difficulty in obtaining large quantities of 3-N-oxide starting material renders this approach to 2-substituted imidazoles particularly undesirable.

Accordingly, there is a clear need in the art for an efficient method for obtaining 2-substituted imidazoles, wherein the starting materials are amenable to large scale synthesis, relatively mild conditions can be used to introduce nucleophilic groups to the 2-position of the imidazoles, and any 3-N-group attached to the imidazole can be easily removed. In particular, there is a clear need in the art for an improved method for obtaining norastemizole.

Citation or identification of any reference in Section 2 of this application shall not be construed as an admission that such reference is available as prior art to the present application.

3. SUMMARY OF THE INVENTION

The present invention provides novel synthetic approaches to preparing 2-substituted imidazoles under relatively mild conditions, which methods provide overall yields of desired product higher than those previously disclosed. In addition, the present invention allows for one-pot syntheses, thereby avoiding isolation or purification of intermediates. Yet another advantage of the present invention is that the final product is highly purified, e.g., free of substantial amounts of undesired side products.

Specifically, the present invention is a method of preparing, e.g., biologically active, 2-substituted imidazoles from readily available imidazoles having a leaving group in the 2-position, which comprises alkylating said imidazole under mild conditions to afford a 3-N-alkylated imidazolium salt; and coupling said imidazolium salt with a nucleophile also under mild conditions to afford a 2-substituted 3-N-alkylated imidazolium salt. This reaction product can optionally be isolated and purified. The 3-N-alkyl group of the 2-substituted 3-N-alkylated imidazolium salt is removed to afford a 2-substituted imidazole.

More specifically, the present invention provides a method for synthesizing a 2-substituted imidazole, comprising the steps of:

(a) reacting an imidazole having a leaving group in the 2-position thereof with an alkylating agent to afford a 3-N-alkylated imidazolium salt having an alkyl group in the 3-N-position and a leaving group in the 2-position thereof;

(b) reacting the 3-N-alkylated imidazolium salt with a nucleophile to afford a 2-substituted 3-N-alkylated imidazolium salt, wherein the nucleophile displaces said leaving group; and (c) removing the alkyl group from the 3-N-position of the 2-substituted 3-N-alkylated imidazolium salt to afford the 2-substituted imidazole.

A preferred method of the present invention comprises:

(a) alkylating a 2-halosubstituted 1-(4-fluorophenylmethyl)-1H-benzimidazole to yield a 3-N-alkylated 2-halosubstituted 1-(4-fluorophenylmethyl)-1H-benzimidazolium salt;

(b) reacting said salt with a 1-N-substituted 4-aminopiperidine to form an adduct; and (c) hydrolyzing said adduct to form norastemizole.

In one embodiment of the invention, the imidazole having a leaving group in the 2-position thereof is a 1-(4-fluorophenylmethyl)-1H-benzimidazole, preferably, 2-chloro-1-(fluorophenylmethyl)-1H-benzimidazole; the alkylating agent is methoxymethyl chloride, bromide or iodide, preferably methoxymethyl bromide; the nucleophile is ethyl 4-amino-1-piperidine carboxylate, 4-N-acetylaminopiperidine or 4-N-trimethylacetylaminopiperidine; and the 2-substituted imidazole is ethyl 4-((1-((4-fluorophenyl)methyl)-1H-benzimidazol-2-yl)amino)-1-piperidine carboxylate.

The present invention provides an additional method for synthesizing 2-substituted imidazoles, using relatively mild reaction conditions, comprising reacting, in the presence of fluoride ion, an imidazole of formula I

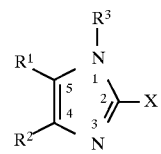

with a nucleophile to afford a 2-substituted imidazole, wherein $R^1$, $R^2$ and $R^3$ are independently hydrogen, $C_1$–$C_{12}$ branched or straight chain alkyl, $C_3$–$C_8$ cycloalkyl, phenyl, naphthyl and benzyl, said $C_1$–$C_{12}$ branched or straight chain alkyl, $C_3$–$C_8$ cycloalkyl, phenyl, naphthyl and benzyl groups being optionally substituted with one or more halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), carboxyl, phenyl, —C(O)O—$C_1$–$C_6$ alkyl or —C(O)$C_1$–$C_6$ alkyl groups, except that $R^3$ is not —C(O)$C_1$–$C_6$ alkyl; or
    either $R^1$ and $R^2$, or $R^1$ and $R^3$, is joined to form a $C_3$–$C_8$ saturated or unsaturated cycloalkyl group, aromatic group, or heteroaromatic group, said $C_3$–$C_8$ saturated or unsaturated cycloalkyl group, aromatic group, or heteroaromatic group being optionally substituted with one or more members of the group consisting of halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), —S(O)$_2$($C_1$–$C_6$ alkyl), carboxyl, phenyl and —C(O)O—$C_1$–$C_6$ alkyl; or $R^1$ and $R^2$ are independently —NHC(O) ($C_1$–$C_6$ alkyl), —N($C_1$–$C_6$ alkyl)C(O) ($C_1$–$C_6$ alkyl), —C(O)NH ($C_1$–$C_6$ alkyl) or —C(O)N($C_1$–$C_6$ alkyl) ($C_1$–$C_6$ alkyl); and X is selected from the group consisting of fluoro, chloro, bromo, iodo, —OSO$_2$CH$_3$, —OSO$_2$CF$_3$, —OSO$_2$C$_6$H$_4$-p-CH$_3$, —OSO$_2$C$_6$H$_4$-p-Br, —OC(O) ($C_1$–$C_6$ alkyl), —N$^+$($C_1$–$C_6$ alkyl) ($C_1$–$C_6$ alkyl) ($C_1$–$C_6$ alkyl) and —S$^+$($C_1$–$C_6$ alkyl) ($C_1$–$C_6$ alkyl), and wherein the nucleophile displaces said leaving group.

The present invention may be understood more fully by reference to the following detailed description and illustrative examples which are intended to exemplify non-limiting embodiments of the invention.

4. DETAILED DESCRIPTION OF THE INVENTION

4.1 SYNTHESIS OF 2-SUBSTITUTED IMIDAZOLES VIA 3-N ACTIVATION OF AN IMIDAZOLIUM SPECIES

4.1.1 GENERAL METHODS

The desired 2-substituted imidazoles of the present invention can be obtained by a process which comprises:

(a) reacting an imidazole having a leaving group in the 2-position thereof with an alkylating agent to afford a 3-N-alkylated imidazolium salt having an alkyl group in the 3-N-position and a leaving group in the 2-position thereof;

(b) reacting the 3-N-alkylated imidazolium salt with a nucleophile to afford a 2-substituted 3-N-alkylated imidazolium salt, wherein the nucleophile displaces said leaving group; and (c) removing the alkyl group from the 3-N-position of the 2-substituted 3-N-alkylated imidazolium salt to afford the 2-substituted imidazole.

An example of this reaction is illustrated in Scheme 1:

Scheme 1

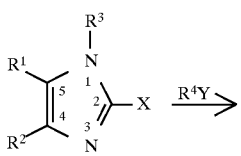

I

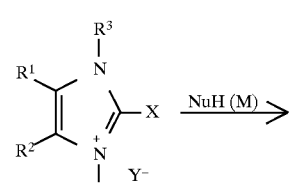

II

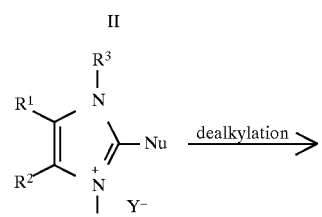

III

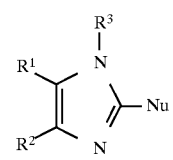

IV

The first step of the process for preparing the 2-substituted imidazoles is to react an imidazole having a leaving group in the 2-position thereof with an alkylating agent to afford a 3-N-alkylated imidazolium salt.

Suitable imidazoles having a leaving group in the 2-position thereof are represented by formula I:

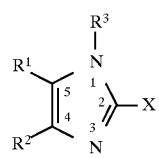

I $R^1$, $R^2$ and $R^3$ can independently be, but are not limited to, hydrogen, $C_1$–$C_{12}$ branched or straight chain alkyl, $C_3$–$C_8$ cycloalkyl, phenyl, naphthyl or benzyl, wherein the $C_1$–$C_{12}$ branched or straight chain alkyl, $C_3$–$C_8$ cycloalkyl, phenyl, naphthyl or benzyl groups are optionally substituted with one or more halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), carboxyl, phenyl, —C(O)O—$C_1$–$C_6$ alkyl and —C(O)$C_1$–$C_6$ alkyl groups, except that $R^3$ is not —C(O)$C_1$–$C_6$ alkyl.

In addition, either $R^1$ and $R^2$, or $R^1$ and $R^3$, can optionally be joined to form a $C_3$–$C_8$ saturated or unsaturated cycloalkyl group, such as for example cyclopropane, cyclobutane, cyclobutene, methylcyclobutane, cyclopentane, cyclopentene, cyclohexane, cyclohexene, methylcyclohexane, dimethylcyclohexane, and the like; aromatic group, such as for example benzene group, toluene group, xylene group and the like; or heteroaromatic group, such as for example thienyl, furyl, 2H-pyrrolyl, imidazolyl, pyrazolyl, pyridyl, pyrazinyl, pyrimidinyl, pyridazinyl, and the like. The cycloalkyl, aromatic and heteroaromatic groups can optionally be substituted with one or more halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), —S(O)$_2$($C_1$–$C_6$ alkyl), carboxyl, phenyl and —C(O)O—$C_1$–$C_6$ alkyl; or $R^1$ and $R^2$ are independently —NHC(O) ($C_1$–$C_6$ alkyl), —N($C_1$–$C_6$ alkyl)C(O) ($C_1$–$C_6$ alkyl), —C(O)NH ($C_1$–$C_6$ alkyl) or —C(O)N($C_1$–$C_6$ alkyl) ($C_1$–$C_6$ alkyl).

Furthermore, $R^1$ and $R^2$ can independently be —NHC(O) ($C_1$–$C_6$ alkyl), —N($C_1$–$C_6$ alkyl)C(O) ($C_1$–$C_6$ alkyl) —C(O)NH($C_1$–$C_6$ alkyl) or —C(O)N($C_1$–$C_6$ alkyl) ($C_1$–$C_6$ alkyl)

Preferably, $R^1$ and $R^2$ are joined to form a benzene group, such that the compound of formula I is a benzimidazole having a leaving group in the 2-position thereof.

It will be understood that when the imidazole having a leaving group in its 2-position bears an $R^1$, $R^2$ or $R^3$ group that has a chiral center, the imidazole having a leaving group in its 2-position can exist either as a single enantiomer, as a racemic mixture of enantiomers, or as a mixture of enantiomers having an enantiomeric excess of either a (+) or (−) enantiomer. Accordingly, the 2-substituted imidazoles obtainable by the present process encompass individual (+) or (−) enantiomers, and mixtures thereof.

It will be further understood that the imidazole having a leaving group in the 2-position thereof can be employed as an acid salt, preferably hydrochloride salt. Acid salts of imidazoles having a leaving group in the 2-position thereof can be prepared by treating the imidazole having a leaving group in the 2-position thereof with desired acids, or by other methods known to those skilled in the art.

In one embodiment of the invention, where $R^3$ is hydrogen, the 1-nitrogen atom of the imidazole is protected by a protecting group prior to reaction with the alkylating agent. Such a protecting group can be subsequently removed, preferably during the hydrolysis step of the present process, or subsequent thereto. Examples of suitable protecting groups, and methods for their addition and removal, can be found in Theodora W. Greene, "Protective Groups in Organic Synthesis," John Wiley & Sons, New York (1981) ("Greene"). When the 1-nitrogen atom of the imidazole is protected with a protecting group, the protecting group is preferably an acyl or alkoxycarbonyl protecting group that is removable via acidic or basic hydrolysis. Alternatively, the 1-nitrogen atom of the imidazole can be protected with an —SO$_2$R group (see T. Fukayama, *Tetrahedron Lett.* 36:6373 (1995)).

It will be understood that an acyl protecting group used to protect an amino group gives rise to an amide moiety. It will further be understood that an alkoxycarbonyl protecting group used to protect an amino group gives rise to a carbamate moiety.

Methods for obtaining imidazoles having a leaving group in the 2-position thereof include halogenation of the corresponding imidazolidone (A. G. Sigfried, CH-4800, Zofinger; R. Gompper et al., *Chem. Ber.* 92:1959 (1928)).

As used herein, "leaving group" means a labile and electron-withdrawing moiety that can be displaced by a nucleophile. Suitable leaving groups, such as "X" as shown above in formula I, include, but are not limited to fluoro, chloro, bromo, iodo, —OSO$_2$CH$_3$, —OSO$_2$CF$_3$, —OSO$_2$C$_6$H$_4$-p-CH$_3$, —OSO$_2$C$_6$H$_4$-p-Br, —OC(O) ($C_1$–$C_6$ alkyl), —N$^+$($C_1$–$C_6$ alkyl) ($C_1$–$C_6$ alkyl) ($C_1$–$C_6$ alkyl) and —S$^+$($C_1$–$C_6$ alkyl) ($C_1$–$C_6$ alkyl).

In one embodiment of the invention, $R^3$ is hydrogen, $R^1$ and $R^2$ are joined together to form a benzene group, and X is a chloro group.

As used herein, "alkylating agent" means a reactive species, having electrophilic properties, that is capable of introducing an "alkyl group" at 3-nitrogen atom of an imidazole, so as to form a relatively stable bond therewith. Illustrative alkylating agents can be represented by the formula $R^4$Y, wherein "$R^4$" is the alkyl group, i.e., the electrophilic portion of the alkylating agent, and "Y" is a leaving group which, upon its departure, enables "$R^4$" to form a relatively stable bond with the 3-nitrogen atom of an imidazole, forming an imidazolium salt.

Suitable $R^4$ groups include, but are not limited to, $R^5$OCH$_2$—, $R^5$OCH$_2$CH$_2$OCH$_2$—, $R^5$SCH$_2$—, ($R^5$)$_3$SiCH$_2$CH$_2$OCH$_2$—, HOCH$_2$CH$_2$—, $R^5$OC(O)—, $R^5$OC(S)—, ($R^5$)($R^5$)NC(O)—, ($R^5$)($R^5$)($R^5$)Si—, ($R^5$)($R^5$)($R^5$)Sn—, ($R^5$)($R^5$)S(O)$_2$CH$_2$—, ($R^5$)($R^5$)S(O)$_2$CH($R^5$)— and ($R^5$)($R^5$)S(O)$_2$C($R^5$)($R^5$)—, wherein each $R^5$ is independently $C_1$–$C_6$ straight or branched chain alkyl, $C_3$–$C_6$ cycloalkyl, ($C_1$–$C_6$ straight or branched chain alkyl)$_3$Si ($C_1$–$C_6$ straight or branched chain alkyl), ($C_3$–$C_6$ cycloalkyl)$_3$Si($C_1$–$C_6$ straight or branched chain alkyl), $C_1$–$C_6$ straight or branched chain alkyl-C(O)— or, when $R^5$ is bonded to a nitrogen atom, $C_1$–$C_6$ straight or branched chain alkyl-OC(O)—. Regardless of the alkylating agent, it is important that the bond formed between the 3-nitrogen atom of the imidazolium salt and the alkyl, e.g., $R^4$ group, be cleavable without disturbing the rest of the imidazolium moiety, or groups optionally substituted thereon.

Suitable Y groups include, but are not limited to, fluoro, chloro, bromo, iodo, —OSO$_2$CH$_3$, —OSO$_2$CF$_3$, —OSO$_2$C$_6$H$_4$-p-CH$_3$, —OSO$_2$C$_6$H$_4$-p-Br, —CN, —O($C_1$–$C_6$ alkyl) and —OC(O) ($C_1$–$C_6$ alkyl).

In a particular embodiment of the invention, $R^4$ is CH$_3$OCH$_2$—, CH$_3$CH$_2$OCH$_2$— or CH$_3$OCH$_2$CH$_2$OCH$_2$— and Y is —Br or —Cl.

The reaction product of the imidazole having a leaving group in the 2-position thereof and the alkylating agent is a 3-N-alkylated imidazolium salt having a leaving group in the 2-position thereof. An illustrative 3-N-alkylated imidazolium salt is shown in Scheme 1, formula II. In other words, the alkylating agent of the present process alkylates the 3-nitrogen atom of the imidazole having a leaving group in the 2-position thereof, converting the imidazole moiety to an imidazolium moiety.

It will be understood that the alkylation of the imidazole having a leaving group in the 2-position thereof with the alkylating agent "activates" the resulting imidazolium moiety to allow a nucleophile to displace the leaving group at the 2-position of the imidazolium salt under relatively mild conditions.

As used herein, "salt" means that the leaving group of the alkylating agent, such as the "Y" group of the $R^4$Y alkylating agent, is available as a counter ion for the imidazolium moiety. It will be understood that prior to reaction of the 3-N-alkylated imidazolium salt with a nucleophile, the leaving group of the alkylating agent, i.e., the counter ion for the imidazolium moiety, can be exchanged for a different counter ion using ion exchange methods known to those skilled in the art.

It is to be noted that in some instances, after the alkylating agent reacts with the imidazole having a leaving group in the 2-position thereof, the leaving group of the alkylating agent can effectively displace the leaving group of the 2-position of the imidazole, such that the leaving group of the alkylating agent becomes the leaving group of the resulting 3-N-alkylated imidazolium salt, and the leaving group of the imidazole becomes the counter ion of 3-N-alkylated imidazolium salt (Scheme 2). Without being bound to any particular theory, it is believed that the displacement of the imidazole leaving group by the leaving group of the alkylating agent occurs via an addition-elimination reaction. It will be understood that in the event that the imidazole leaving group is displaced by the leaving group of the alkylating agent, the resulting imidazolium salt will be at least as reactive toward a nucleophile as if the imidazole leaving group is not displaced by the leaving group of the alkylating agent.

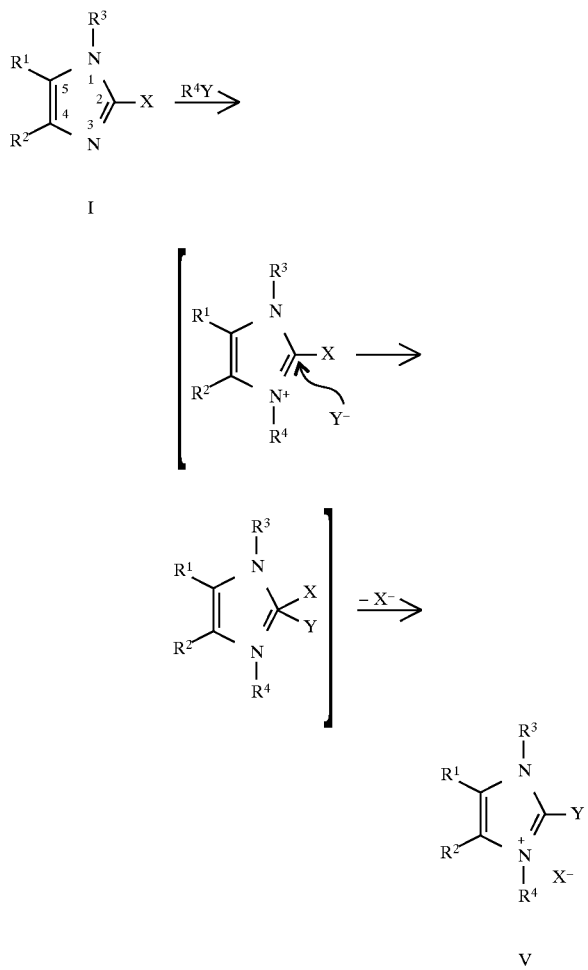

The reaction of the imidazole having a leaving group in the 2-position thereof with the alkylating agent is conducted in an organic solvent including, but not limited to, diethyl ether, ethyl acetate, tetrahydrofuran, benzene, chlorobenzene, dichlorobenzene, toluene, xylene, dichloromethane, and the like, including mixtures thereof, at a temperature from about −78° C. to about 40° C., preferably from about 0° C. to about 25° C. In a preferred embodiment of the invention, the organic solvent used for the reaction of the imidazole having a leaving group in the 2-position thereof and the alkylating agent is toluene, and the reaction temperature is between about 20°–25° C. The course of the reaction can be measured spectroscopically, using, for example, high performance liquid chromatography ("HPLC"). Typically, the reaction is performed over the course of about 10 minutes to about 24 hours, preferably, over the course of about 0.5 hours to about 2 hours. In addition, the reaction is typically performed at atmospheric pressure, preferably under a $N_2$ atmosphere.

In some instances, the resulting 3-N-alkylated imidazolium salt will be insoluble in the reaction solvent and accordingly, can be isolated merely by filtration, preferably by vacuum filtration. In these instances, it may be preferable to wash the isolated 3-N-alkylated imidazolium salt with fresh organic solvent of the same type used in the reaction to form the 3-N-alkylated imidazolium salt. In other instances, however, depending upon the polarity of the 3-N-alkylated imidazolium salt product and the selected organic solvent used in the reaction to form the 3-N-alkylated imidazolium salt, the 3-N-alkylated imidazolium salt can be soluble in the selected organic solvent. In this instance, the resulting solution of 3-N-alkylated imidazolium salt and organic solvent can be concentrated, optionally in vacuo, to obtain the 3-N-alkylated imidazolium salt, which can be used in the next step of the synthesis without further purification. If further purification is desired, the resulting 3-N-alkylated imidazolium salt can be purified by recrystallization, or by other means or methods known to those skilled in the art.

In the next step of the invention, the 3-N-alkylated imidazolium salt is reacted with a displacement nucleophile to afford a 2-substituted 3-N-alkylated imidazolium salt, i.e., an "adduct" of the reaction between the displacement nucleophile and the 3-N-alkylated imidazolium salt having a leaving group in the 2-position thereof. As used herein, "displacement nucleophile" means any species that is capable of displacing a leaving group from the 2-carbon atom of a compound of formula I or formula II, and forming a relatively stable bond with the 2-carbon atom thereof. It will be understood that reaction of the 3-N-alkylated imidazolium salt with the displacement nucleophile does not result in the removal of the alkyl group of the 3-nitrogen atom of the imidazolium species, to any significant degree.

Suitable displacement nucleophiles include, but are not limited to, $NH_3$, $NH_2(C_1-C_6$ alkyl), $NH_2(C_3-C_8$ cycloalkyl), $NH_2$(phenyl), $NH_2$(Het), $NH(C_1-C_6$ alkyl) $(C_1-C_6$ alkyl), NH(phenyl) $(C_1-C_6$ alkyl), NH(Het) $(C_1-C_6$ alkyl), NH(phenyl) (phenyl), NH(phenyl) (Het), NH(Het) (Het), $NH_2NH_2$, $MN_3$, $HO(C_1-C_6$ alkyl), $HO(C_1-C_6$ alkenyl), $HO(C_1-C_6$ alkynyl), $HO(C_3-C_8$ cycloalkyl), $HO(C_3-C_8$ cycloalkenyl), $HS(C_1-C_6$ alkyl), $HS(C_1-C_6$ alkenyl), $HS(C_1-C_6$ alkynyl), $HS(C_3-C_8$ cycloalkyl), $HS(C_3-C_8$ cycloalkenyl), HO-phenyl, HO-naphthyl, MSi $(C_1-C_6$ alkyl) $(C_1-C_6$ alkyl) $(C_1-C_6$ alkyl), $(C_1-C_6$ alkyl) Mg(halogen), $(C_1-C_6$ alkenyl)Mg(halogen), $(C_1-C_6$ alkyl) Li, $(C_1-C_6$ alkenyl)Li, $(C_1-C_6$ alkyl$)_2$Zn, $(C_1-C_6$ alkenyl$)_2$Zn, $(C_1-C_6$ alkyl)CeCl$_2$, $MZn(C_1-C_6$ alkyl) $(C_1-C_6$ alkyl) $(C_1-C_6$ alkyl), $Br^-$, $I^-$, $F^-$, $MP(C_1-C_6$ alkyl$)_2$, $HP(C_1-C_6$ alkyl$)_2$, $H_2N(C_1-C_6$ alkyl), $H_2N(C_1-C_6$ alkenyl) and $H_2N$ $(C_1-C_6$ alkynyl);

wherein M is $Na^+$ $Li^+$, $K^+$ $^+Mg$(halogen), $^+Mn$(halogen), $^+Zn$(halogen), $^+Sn$(halogen), each Het is independently 2-pyrrolyl, 3-pyrrolyl, 2-imidazolyl, 4-imidazolyl, 5-imidazolyl, 3-pyrazolyl, 4-pyrazolyl, 5-pyrazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 3-isoxazolyl, 4-isoxazolyl, 5-isoxazolyl, 3-isothiazolyl, 4-isothiazolyl, 5-isothiazolyl, 2-imidazolidinyl, 4-imidazolidinyl, 3-pyrazolidinyl, 4-pyrazolidinyl, 2-piperidinyl, 3-piperidinyl, 4-piperidinyl, 2-piperazinyl, 3-piperazinyl, 4-piperazinyl, 2-morpholinyl or 3-morpholinyl, and the displacement nucleophiles can be optionally substituted, at either a carbon atom or a heteroatom, such as nitrogen, with one or more halogen, hydroxyl, sulfhydryl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl)($C_1$–$C_6$ alkyl), carboxyl, phenyl, $C_1$–$C_6$ alkoxylcarbonyl and ($C_1$–$C_6$ alkyl)-CO groups.

The displacement nucleophiles can be obtained commercially or via conventional organic synthesis by methods known to those skilled in the art.

In one embodiment of the invention, the displacement nucleophile is ethyl 4-amino-1-piperidine carboxylate. In another embodiment of the invention, the displacement nucleophile is 4-N-acetylaminopiperidine. In still another embodiment of the invention, the displacement nucleophile is 4-N-trimethylacetylaminopiperidine.

An illustrative 2-substituted 3-N-alkylated imidazolium salt is show in formula III, Scheme 1.

It will be understood that when the displacement nucleophile comprises an amino, an alkoxy, or a thioalkoxy group, the displacement nucleophile can optionally be in the form of its sodium, calcium, silver, lithium, potassium, magnesium, cerium, manganese, zinc or tin salt. Such salts are readily prepared by methods known to those skilled in the art.

The displacement nucleophile can comprise more than one "nucleophilic" groups, i.e., the displacement nucleophile can comprise more than one amino groups, more that one hydroxyl groups, more than one sulfhydryl groups, combinations of amino, hydroxyl and sulfhydryl groups, and so on. In this instance, at least one protecting group can be used to protect any other "nucleophilic" species of the displacement nucleophile that is not desired to form a bond with the 3-carbon atom of the imidazolium species. When the displacement nucleophile has more than one nucleophilic groups, and one of the nucleophilic groups that is not desired to form a bond with the 3-carbon atom of the imidazolium species is an amino group, the protecting group for that amino group is preferably an amide or a carbamate protecting group. Suitable protecting groups, and methods for their addition and removal, are found in Greene, supra. Accordingly, a 2-substituted 3-N-alkylated imidazolium salt that is obtained from the reaction of the 3-N-alkylated imidazolium salt and a displacement nucleophile that has a protecting group, necessarily comprises a protecting group that resides on the portion of the displacement nucleophile that does not form a bond with the carbon atom at the 2-position of the 3-N-alkylated imidazolium salt.

Where the displacement nucleophile is 4-aminopiperidine, and it is desired that the primary amino group thereof form a bond with the 2-carbon of the imidazolium salt, the displacement nucleophile is a 1-N-protected 4-aminopiperidine. The protecting group for the piperidine nitrogen atom is one found in Greene, supra; a sulfonyl group such as optionally substituted alkyl and benzenesulfonyl groups, e.g., p-toluenesulfonyl, methanesulfonyl, trifluoromethanesulfonyl, p-methoxybenzenesulfonyl, o-nitrobenzenesulfonyl, and the like; an acid labile alkyl group such as a methoxymethyl, 2-methoxyethoxymethyl, 2-(trimethylsilyl)ethoxymethyl, 2-tetrahydropyranyl, 2-tetrahydrofuranyl, $(CH_3)_3SiCH_2CH_2$— or $Ph_3C$—; or preferably, an acyl or alkoxycarbonyl protecting group. Where the protecting group is an acyl protecting group, the protecting group is preferably an acetyl or trimethylacetyl protecting group. Where the protecting group is an alkoxycarbonyl protecting group, the protecting group is preferably an ethoxycarbonyl protecting group.

The reaction of the 3-N-alkylated imidazolium salt with the displacement nucleophile is conducted in an organic solvent including, but not limited to, methylene chloride, chloroform, diethyl ether, tetrahydrofuran, benzene, chlorobenzene, dichlorobenzene, toluene, xylene, dimethyl sulfoxide, dimethylformamide and the like, and mixtures thereof, and at a temperature from about 0° C. to about reflux temperatures, preferably from about 25° C. to about 60° C. Preferably, the reaction is performed at atmospheric pressure, optionally under a blanket of inert gas such as $N_2$. In a preferred embodiment of the invention, the organic solvent used for the reaction of the 3-N-alkylated imidazolium salt and the displacement nucleophile is toluene, at a reaction temperature of about 50° C. The course of the reaction can be measured spectroscopically, using, for example, HPLC. The resulting 2-substituted 3-N-alkylated imidazolium salt can optionally be purified by recrystallization.

Without being bound to any particular theory, it is believed that the displacement of the 3-N-alkylated imidazolium salt leaving group by the displacement nucleophile occurs via an addition-elimination reaction (Scheme 3). Such a reaction is particularly advantageous since the leaving group at the 2-position of the 3-N-alkylated imidazolium salt can be displaced by the displacement nucleophile under relatively mild conditions.

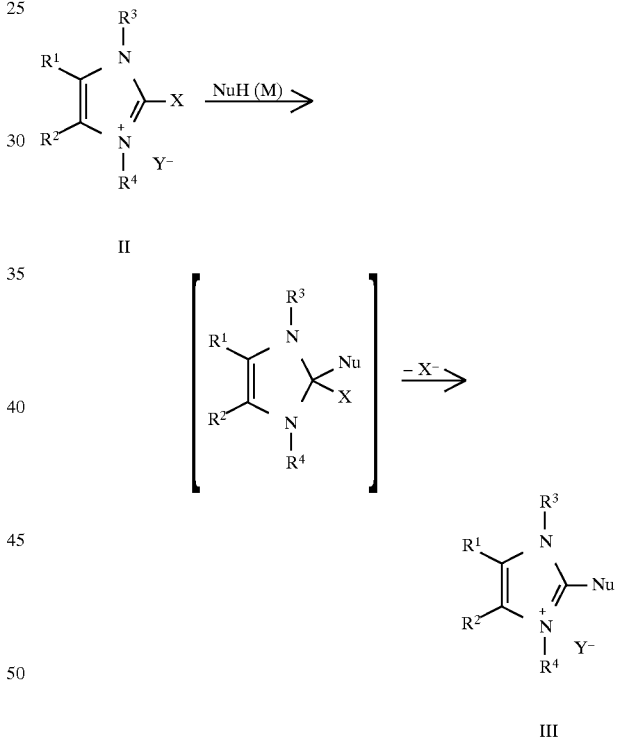

Scheme 3

It is to be pointed out that because the leaving group displaced by the displacement nucleophile becomes released into the reaction media, in some instances, the ion form of the leaving group, such as "Y$^-$", can be the counter ion of the 2-substituted 3-N-alkylated imidazolium salt. In this instance, the resulting imidazolium salt will be at least as susceptible to nucleophilic deprotection as if the counter ion of the 2-substituted 3-N-alkylated imidazolium salt was derived from the leaving group of the alkylating agent.

It is to be further pointed out that the 2-substituted 3-N-alkylated imidazolium salts of the present invention, e.g., the compound of formula III, are relatively stable to air, and can be stored at ambient temperature for at least several months.

In the final step of the present process, the alkyl group is removed from the 3-N-position of the 2-substituted 3-N-alkylated imidazolium salt to afford the 2-substituted imidazole. This step can involve either hydrolytic or nucleophilic dealkylation. Such hydrolytic and nucleophilic dealkylation reactions useful for removing the alkyl group from 3-N-position of the 2-substituted 3-N-alkylated imidazolium salt are collectively referred to herein as "dealkylation reactions."

The dealkylation reaction removes the alkyl group, e.g., the $R^4$ group, from the 3-N-alkylated imidazolium salt, so as to provide the 2-substituted imidazole or a 3-N imidazolium salt form thereof. The 3-N imidazolium salt form of the 2-substituted imidazole can be obtained when the dealkylation reaction is a hydrolytic dealkylation reaction performed using acidic conditions. As used herein, "dealkylation reaction" is meant to encompass reaction conditions sufficient to remove the alkyl group from the 3-position of the 2-substituted 3-N-alkylated imidazolium salt, without affecting, e.g., hydrolyzing or otherwise modifying, the imidazolium moiety, per se, other than optionally removing protecting groups from the displacement nucleophile portion of the 2-substituted 3-N alkylated imidazolium salt moieties. It will be understood that the 2-substituted imidazole obtained by the present process is unsubstituted, i.e., bears a hydrogen atom, at the 3-N-position of the imidazole. It will be further understood that in this context, "unsubstituted" encompasses 3-N imidazolium salts.

In the case of hydrolytic dealkylation, typical dealkylation reactions are those involving the use of water and an acid catalyst, or in the case of nucleophilic dealkylation, a dealkylating nucleophile such as pyridine, thiolates, triethylamine, ammonia, iodide ion, thiocyanate ion and bromide ion, in an amount sufficient to remove the alkyl group from the 3-position of the 2-substituted 3-N-alkylated imidazolium salt, without affecting, e.g., hydrolyzing or otherwise modifying, the imidazolium moiety, per se. However, if the imidazolium moiety is substituted with a group that bears a protecting group, in particular, a displacement nucleophile having one or more nucleophilic groups, the dealkylation reaction can effect removal of such a protecting group, as long as the protecting group is removable under the conditions of the dealkylation reaction. In this instance, the dealkylation reaction conveniently accomplishes two transformations, i.e., removal of the alkyl group from the 3-N position of the imidazolium moiety, and removal of a protecting group located on a group with which the imidazolium moiety is substituted. In the case where the imidazolium moiety is substituted with a group that bears a protecting group, and it is desired to remove that protecting group, but that protecting group is not cleavable under the conditions of the dealkylation reaction, a subsequent step of removing that protecting group may be required.

Where the dealkylation reaction is a hydrolytic dealkylation reaction that involves the use of an acid catalyst, the resulting 2-substituted imidazole product can be in form of its 3-N-imidazolium salt. In this instance, the product of the dealkylation reaction is a 2-substituted 3-imidazolium acid salt. It will be understood that in this context, "acid salt" is meant a compound wherein the 2-substituted imidazole forms an ionic bond at the 3-nitrogen atom thereof, with a proton preferably derived from the acid catalyst, wherein the counter ion of the resulting 2-substituted 3-imidazolium acid salt is the conjugate base of the acid catalyst. The 2-substituted 3-imidazolium acid salt can be converted to its free base, i.e., the 2-substituted imidazole, by washing the 2-substituted 3-imidazolium and salt with an aqueous solution of a base, preferably a saturated aqueous solution of sodium bicarbonate, sodium carbonate or dilute sodium hydroxide; and optionally extracting the resulting free base into an organic solvent which can be concentrated to provide the free base. General methods for converting amine salts to free bases are well known to those skilled in the art.

Where the alkylating agent is a methoxymethyl halide, such as for example, a methoxymethyl or 2-methoxyethoxymethyl halide, the dealkylation can be a hydrolytic dealkylation reaction that preferably involves the use of a boron trihalide, preferably boron tribromide, and a mineral acid, such as hydrobromic acid or hydrochloric acid. In a further embodiment of the invention, where the alkylating agent is a methoxymethyl or 2-methoxyethoxymethyl halide, the hydrolytic dealkylation reaction involves the use of hydroxide, such as for example, potassium hydroxide, in alcoholic solvent, such as for example, aqueous ethanol.

Where a boron trihalide is employed in the dealkylation reaction, treatment of the 2-substituted 3-N-alkylated imidazolium salt affords an intermediate dealkylation product which gets hydrolyzed to provide the 2-substituted imidazole. Boron trihalide treatment of the 2-substituted 3-N-alkylated imidazolium salt can occur at from about 0° C. to about 50° C., preferably from about 20° C. to about 30° C., in a reaction solvent including, but not limited to methylene chloride, chloroform, benzene, toluene, xylene, dimethyl sulfoxide and the like. Preferably, the boron trihalide is $BBr_3$, and the reaction solvent is methylene chloride.

The intermediate dealkylation product is hydrolyzed, preferably using concentrated mineral acid, and most preferably using 48% hydrobromic acid or 18–36%, preferably 25%, hydrochloric acid. The hydrolysis of the dealkylation product occurs at a temperature from about 25° C. to about 125° C., preferably from about 50° C. to about 125° C., and most preferably from about 100° C. to about 115° C. Following hydrolysis, the resulting 2-substituted 3-N imidazolium acid salt is optionally isolated, or preferably washed with an aqueous solution of base as described above, and purified either by silica gel chromatography or high performance liquid chromatography, or preferably, via recrystallization.

Where the alkylating agent is a methoxymethyl or 2-methoxyethoxymethyl halide, such as for example, methoxymethyl bromide or 2-methoxyethoxymethyl chloride, the dealkylation reaction can be a nucleophilic dealkylation reaction (see E. J. Grabowski et al., *J. Med. Chem.* 17(5) :547–49 (1974)). Nucleophiles useful for dealkylating an alkyl group, in particular, a methoxymethyl or 2-methoxyethoxymethyl group from the 3-N position of the 2-substituted 3-N-alkylated imidazolium salt include amines such as pyridine, 4-dimethylaminopyridine, lutidine, collidine, methylamine, diisopropylethylamine, di-tert-butylamine, triethylamine, ammonia, and the like; and ionic dealkylating nucleophiles such as chloride, bromide, iodide ion, thiocyanate, and the like. Preferably, the dealkylating nucleophile(s) used in the nucleophilic dealkylation reaction is (are) pyridine, 4-dimethylaminopyridine or a mixture thereof.

The nucleophilic dealkylation reaction can be performed in a suitable reaction solvent or, in the case where the dealkylating nucleophile itself can function as a solvent, e.g., where the dealkylating nucleophile is an amine, the nucleophilic dealkylation reaction can be performed neat. Preferably, the nucleophilic dealkylation reaction is performed with an excess of dealkylating nucleophile.

Nucleophilic dealkylation reactions can be performed from about at room temperature to about 120° C., preferably from about 40° C. to about 100° C.

In some cases, the displacement nucleophile can have one or more nucleophilic groups. By "nucleophilic groups" is meant functional groups that are capable of displacing a leaving group from the 2-carbon atom of a 3-N-alkylated imidazolium salt, and forming a relatively stable bond with the 2-carbon atom of a 3-N-alkylated imidazolium salt. Where the displacement nucleophile has more than one nucleophilic group, a protecting group can be used to protect those nucleophilic groups of the displacement nucleophile that are desired not to form a bond with the 3-carbon atom of the imidazolium species. In this instance, those protecting groups can be removed in the dealkylation step. Where it is desired that such protecting groups be removed in the dealkylation step, it is important that the chosen protecting groups are removable under the reaction conditions used to remove the alkyl group from the 3-position of the 2-substituted 3-N-alkylated imidazolium salt.

If the protecting group(s) of the displacement nucleophile is (are) not removable under the conditions used to remove the alkyl group from the 3-position of the 2-substituted 3-N-alkylated imidazolium salt, a subsequent hydrolysis step, or any other step useful for removing the protecting group(s), may be required.

In a preferred embodiment of the invention, where the displacement nucleophile is 4-aminopiperidine, the displacement nucleophile is a 1-N-protected 4-aminopiperidine. The protecting group for the piperidine nitrogen atom is an alkoxycarbonyl group, such as for example, methoxy, 9-fluorenylmethoxy, ethoxy, 2,2,2-trichloroethoxy, 2-trimethylsilylethoxy, 1,1-dimethylpropynoxy, 1-methyl-1-phenylethoxy, 1,1-dimethyl-2-haloethoxy, 1,1-dimethyl-2-cyanoethoxy, t-butoxy, cyclobutoxy, 1-methylcyclobutoxy, 1-adamantyloxy, vinyloxy, allyloxy, cinnamyloxy, 8-quinolyloxy, N-hydroxypiperidinyloxy, benzyloxy, p-nitrobenzyloxy, 3,4-dimethoxy- 6-nitrobenzyloxy, 2,4-dichlorobenzyloxy and diphenylmethoxy carbonyl, and the like or, the protecting group for the piperidine nitrogen atom is an acyl group. Most preferably, the alkoxycarbonyl group is an ethoxycarbonyl group, and the acyl group is an acetyl or trimethylacetyl group. Suitable 1-N-protected 4-aminopiperidines are obtained, for example, by first reacting a 4-piperidone, preferably in the form of its hydrate hydrochloride, with an acid chloride or an alkoxycarbonyl chloride, to provide a 4-N-protected piperidone which, following treatment with hydroxylamine and then with hydrogen in the presence of a suitable hydrogenation catalyst, preferably $PtO_2$, affords the 1-N-protected 4-aminopiperidine. It is to be pointed out that ethyl 4-amino-1-piperidinecarboxylate can be purchased commercially from, for example, Aldrich Chemical Co., Milwaukee, Wis. In another embodiment of the invention, the protecting group for the 4-aminopiperidine displacement nucleophile is an acyl group, preferably an acetyl or trimethylacetyl group. Other protecting groups, and methods for their addition and removal, are found in Greene, supra.

Where the primary amino group of 4-aminopiperidine is sought to form a bond with the 2-carbon atom of an imidazolium salt, and an alkoxycarbonyl group, in particular an ethoxycarbonyl group, or an acyl group, in particular an acetyl or a trimethylacetyl group is employed as a protecting group for the piperidine nitrogen atom of 4-aminopiperidine, the dealkylation reaction used to remove the alkyl group from the 3-position of the 2-substituted 3-N-alkylated imidazolium salt may, in certain instances, be ineffective for removing the alkoxycarbonyl or acyl protecting group. In these cases, the alkoxycarbonyl or acyl protecting group can be removed by treatment with base, preferably hydroxide base at a pH from about 9 to about 14, and most preferably from about 10 to about 12, at a temperature from about 50° C. to about 85° C., for about 10 minutes to about 24 hours, preferably for about 30 minutes to about 15 hours, and most preferably for about 2 to about 10 hours. Alternatively, the alkoxy carbonyl or acyl protecting group of can be removed via acid hydrolysis, using concentrated, i.e., at least 5M, mineral acid (pH 0-1). However, when the protecting group is a trimethylacetyl group, the trimethylacetyl group cannot be removed by treatment with base.

In an alternate embodiment of the invention, either prior or subsequent to reaction of the alkylating agent with the imidazole having a leaving group in the 2-position, the imidazole can be selectively alkoxycarbonylated or sulfonylated at the 1-position so as to afford, following alkylation with the alkylating agent, a 1-N-alkoxycarbonyl- or 1-N-sulfonyl-3-N-alkylated imidazolium salt. It will be understood that in this case, the imidazole used in the alkoxycarbonylation or sulfonylation reaction be unsubstituted in the 1-position. The 1-N-alkoxycarbonyl or 1-N-sulfonyl-3-N-alkylated imidazolium salt is "doubly activated" in that in addition to having a 3-N alkyl group, it also bears a 1-N-alkoxycarbonyl or -sulfonyl group which withdraws electron density from the imidazolium nucleus group, thereby increasing its electrophilicity at the 2-position. Accordingly, the presence of the 1-N-alkoxycarbonyl or -sulfonyl group accelerates the rate of reaction between the 1-N-alkoxycarbonyl- or 1-N-sulfonyl-3-N-alkylated imidazolium salt and the displacement nucleophile.

Following reaction of the displacement nucleophile with the 1-N-alkoxycarbonyl- or 1-N-sulfonyl-3-N-alkylated imidazolium salt, the 1-N-alkoxycarbonyl or -sulfonyl group is removed. Advantageously, the 1-N-alkoxycarbonyl or -sulfonyl group is removed during the dealkylation step or alternatively, if the displacement nucleophile has a protecting group that is not removable under conditions used to remove the 3-N-alkyl group, the 1-N-alkoxycarbonyl or -sulfonyl group can be removed in a subsequent step.

Useful alkoxycarbonyl groups are typically $C_1$–$C_6$ alkoxycarbonyl groups. Preferably, the $C_1$–$C_6$ alkoxycarbonyl group is a tert-butoxycarbonyl group. Typically, alkoxycarbonylation occurs via treatment with a corresponding alkyl haloformate, preferably an alkyl chloroformate, preferably in the presence of base, such as for example a metal carbonate or bicarbonate, or an organic amine. Useful sulfonyl groups are optionally substituted alkyl and benzenesulfonyl groups, such as for example, p-toluenesulfonyl, methanesulfonyl, trifluoromethanesulfonyl, p-methoxybenzenesulfonyl, o-nitrobenzenesulfonyl, and the like. Typically, sulfonylation can occur via treatment with a sulfonyl halide, preferably in the presence of base, such as for example a metal carbonate or bicarbonate, or an organic amine. Methods of addition and removal of alkoxycarbonyl and sulfonyl groups are well known in the art. Examples of addition and removal of alkoxycarbonyl and sulfonyl groups can be found in Greene, supra. When the sulfonyl group is a p-toluenesulfonyl group, the sulfonyl group is preferably removed with a mixture of 2 eq. of $HSCH_2CO_2H$ and excess LiOH, most preferably in dimethyl formamide solvent, and at temperature of about 40° C. to about 80° C., preferably about 50° C. to about 60° C., for about 2 minutes to about 15 minutes, preferably for about 5 to about 10 minutes.

Following removal of the alkoxycarbonyl or sulfonyl group, the 1-position of the imidazole moiety can be functionalized, preferably alkylated via conventional alkylation techniques. In a preferred embodiment, the 1-position of the imidazole moiety is alkylated with a benzyl halide, preferably 4-fluorobenzyl bromide. In the preferred embodiment, the benzylation reaction is performed in the presence of excess base, preferably a metal hydroxide and most preferably, potassium hydroxide. In addition, the benzylation reaction preferably is performed in a polar organic solvent, preferably dimethylformamide, at a temperature of about room temperature to about 100° C., preferably from about 40° C. to about 60° C., for about 1 minute to about 6 hours, preferably from about 1 minute to about 3 hours.

4.1.2 SYNTHESIS OF NORASTEMIZOLE VIA 3-N ALKYLATION OF A BENZIMIDAZOLE

Also encompassed by this invention is a method for the synthesis of norastemizole. This method can be illustrated below in Scheme 4:

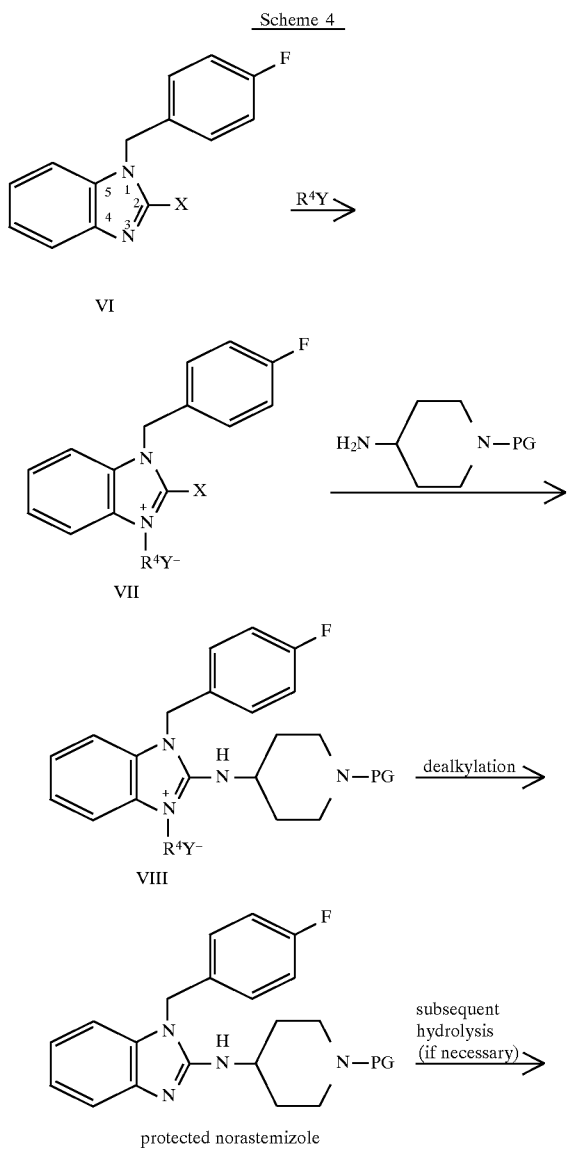

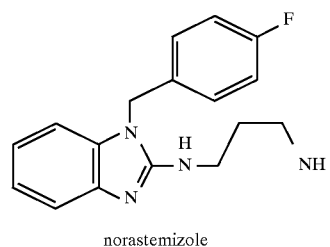

norastemizole

The synthesis involves the alkylation of a 1-(4-fluorophenylmethyl)-1H-benzimidazole having a leaving group in the 2-position thereof (a "compound of formula VI"),

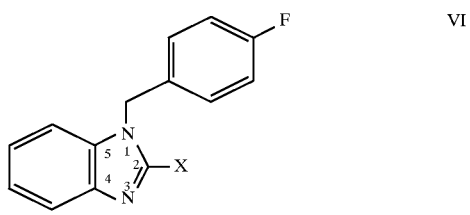

wherein X is a leaving group, with alkylating agent to afford a 3-N-alkylated 1-(4-fluorophenylmethyl)-1H-benzimidazolium salt having a leaving group in the 2-position thereof (a "compound of formula VII"):

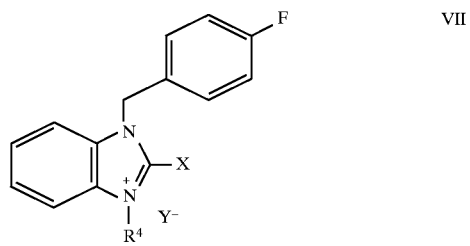

Suitable leaving groups "X" include, but are not limited to, those defined above for "X" in Section 4.1.1.

Compounds of formula VI, such as for example 2-chloro-1-(4-fluorophenylmethyl)-1H-benzimidazole, can be obtained commercially from Siegfried AG, CH-4800, Zofingen, or from Lancaster Synthesis Inc., Windham, N.H.; or by halogenation of the corresponding imidazolidone (R. Gompper et al., *Chem. Ber.* 92:1959 (1928)).

It is to be understood that the compound of formula VI can be in the form of its acid salt, preferably hydrochloride salt, form. Acid salts of the compound of formula VI are obtained by methods useful for obtaining acid salts of an imidazole having a leaving group in the 2-position thereof, discussed in Section 4.1.1 above.

As mentioned above, by "alkylating agent" is meant a reactive species, having electrophilic properties, that is capable of forming a relatively stable bond with the 3-nitrogen atom of the compound of formula VI. Illustrative alkylating agents can be represented by the formula $R^4Y$, wherein "$R^4$" is the alkyl group, i.e., the electrophilic portion of the alkylating agent, and "Y" is a leaving group which, upon its departure, enables "$R^4$" to form a relatively stable bond with the 3-nitrogen atom of the compound of formula VI, forming a benzimidazolium salt, i.e., the compound of formula VII.

Suitable $R^4$ and Y groups include, but are not limited to, those defined in Section 4.4.1, above. Regardless of the alkylating agent, it is important that the bond formed between the 3-nitrogen atom of the compound of formula VI and the alkyl, e.g., $R^4$ group, be hydrolytically cleavable without disturbing the rest of the benzimidazolium moiety of the compound of formula VII.

The reaction product of the compound of formula VI and the alkylating agent is the compound of formula VII. In other words, the alkylating agent of the present process alkylates the 3-nitrogen atom of the compound of formula VI, converting the benzimidazole moiety thereof to an benzimidazolium moiety. The leaving group of the alkylating agent, e.g., the "Y" group of $R^4Y$, is available as a counter ion for the benzimidazolium moiety. It will be understood that prior to reaction of the compound of formula VII with a 4-amino-1-N-protected piperidine, the leaving group of the alkylating agent, i.e., the counter ion for the benzimidazolium moiety, can be exchanged for a different counter ion using ion exchange methods known to those skilled in the art.

It is to be pointed out that in some instances, after the alkylating agent reacts with the compound of formula VI, the leaving group of the alkylating agent can effectively displace the leaving group of the 2-position of the compound of formula VI, such that the leaving group of the alkylating agent becomes the leaving group of the resulting compound of formula VI, and the leaving group of the compound of formula VI becomes the counter ion of the compound of formula VII (Scheme 5). Without being bound to any particular theory, it is believed that the displacement of the leaving group of the compound of formula VI by the leaving group of the alkylating agent occurs via an addition-elimination reaction. It will be understood that in the event that the benzimidazole leaving group is displaced by the leaving group of the alkylating agent, the resulting benzimidazolium salt will be at least as reactive toward a displacement nucleophile as if the benzimidazolium leaving group is not displaced by the leaving group of the alkylating agent.

Scheme 5

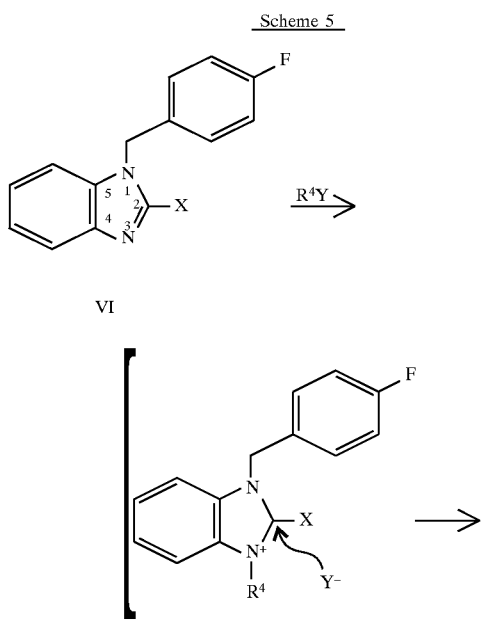

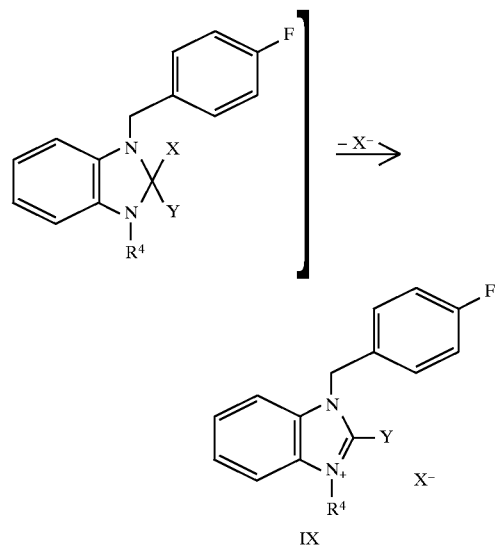

In the next step of the present process, the compound of formula VII is reacted with a 4-amino-1-N-protected piperidine to afford a 2-(4-amino-1-N-protected piperidinyl)-substituted 3-N-alkylated 1-(4-fluorophenylmethyl)-1H-benzimidazolium salt (the "compound of formula VIII"). The 4-amino-1-N-protected piperidine is a 4-aminopiperidine that has a protecting group, removable via hydrolysis, on the 1-nitrogen atom thereof. Suitable protecting groups, and methods for their removal, are found in Greene, supra, and can include sulfonyl groups such as optionally substituted alkyl and benzenesulfonyl groups, e.g., p-toluenesulfonyl, methanesulfonyl, trifluoromethanesulfonyl, p-methoxybenzenesulfonyl, o-nitrobenzenesulfonyl, and the like; an acid labile alkyl group such as a methoxymethyl, 2-methoxyethoxymethyl, 2-(trimethylsilyl)ethoxymethyl, 2-tetrahydropyranyl, 2-tetrahydrofuranyl, $(CH_3)_3SiCH_2CH_2$— or $Ph_3C$—; and preferably, an acyl or alkoxycarbonyl protecting group. Where the protecting group is an acyl protecting group, the protecting group is preferably an acetyl or trimethylacetyl protecting group. Where the protecting group is an alkoxycarbonyl protecting group, the protecting group is preferably an ethoxycarbonyl protecting group. Preferably, the protecting group is an acyl or alkoxycarbonyl protecting group such as one defined in Section 4.1.1 above. Most preferably, the protecting group is an ethoxycarbonyl group, an acetyl group or a trimethylacetyl group, on the 1-nitrogen atom of the piperidine moiety.

It will be understood that reaction of the compound of formula VII with the 4-amino-1-N-protected piperidine does not result in the removal of the alkyl group of the 3-nitrogen atom of the benzimidazolium species, to any significant degree.

In the final step of the present process, the compound of formula VIII is dealkylated at the 3-N position to afford protected norastemizole. As used herein, "protected norastemizole" refers to norastemizole or a norastemizole derivative having a protecting group on the nitrogen atom of the piperidine moiety thereof. In this step, a dealkylation reaction removes the alkyl group, e.g., the $R^4$ group, from the compound of formula VIII, so as to provide protected norastemizole or a 3-N acid salt thereof. Useful dealkylation reactions are those described in Section 4.1.1, above.

In a preferred embodiment of the invention, the protecting group for 4-amino-1-N-protected piperidine and accordingly, protected norastemizole, is an acyl or alkoxycarbonyl protecting group. When the protecting group is an acyl protecting group, the protecting group is preferably an acetyl or trimethylacetyl protecting group. When the protecting group is an alkoxycarbonyl protecting group, the protecting group is preferably an ethoxycarbonyl group.

The 4-amino-1-N-protected piperidines useful as displacement nucleophiles can be prepared as follows: 4-Piperidone, optionally in the form of its hydrate acid salt, is treated with the acid chloride or alkyl chloroformate corresponding to the desired acyl or alkoxycarbonyl protecting group. Methods for N-acylation and N-(alkoxy)carbonylation are known to those skilled in the art; however, such N-acylation and N-(alkoxy)carbonylation reactions are advantageously performed in the presence of a chlorinated hydrocarbon solvent, preferably methylene chloride, and in the presence of an excess of an amine base. Useful amine bases include, but are not limited to, triethylamine, diisopropylethylamine, pyridine, 4-dimethylaminopyridine, and mixtures thereof. The reaction of the acid chloride or the alkylchloroformate and the 4-piperidone generally proceeds at a temperature of between about 0° C. and about 60° C., preferably at about room temperature and 45° C.

The resulting N-protected 4-piperidone is treated with hydroxylamine, preferably in the presence of alcoholic solvent, most preferably in methanol, and preferably in the presence of a metal carbonate or bicarbonate, most preferably sodium carbonate, to form an oxime. The reaction of the N-protected 4-piperidone and hydroxylamine generally proceeds at a temperature of between about 0° C. and about 60° C.

The resulting oxime is hydrogenated with hydrogen gas in the presence of a Pt or Pd catalyst, preferably a Pt catalyst and most preferably $PtO_2$, to afford the 4-amino-1-N-protected piperidine. Advantageously, the hydrogenation reaction is performed under pressure, e.g., at a pressure of about 25 to about 75 psi. Such hydrogenation reactions are, in general, mostly complete within several days.

Alternatively, the acyl or alkoxycarbonyl protecting group can be installed by first protecting the 4-amino group of the 4-aminopiperidine with, for example, an acid-labile protecting group, e.g., a benzylidene protecting group, followed by reaction with ethyl chloroformate in the presence of excess base, e.g., pyridine, optionally in the presence of catalytic 4-dimethylaminopyridine. In addition, ethyl 4-amino-1-piperidinecarboxylate can be purchased commercially from, for example, Aldrich Chemical Co., Milwaukee, Wis. Other protecting groups, and methods for their addition and removal, are found in Greene, supra.

The dealkylation reaction used to remove the alkyl group from the compound of formula VIII may, in certain instances, be ineffective for removing the protecting group of the displacement nucleophile. Where the dealkylation reaction involves acid hydrolysis, the product of dealkylation of the compound of formula VIII can be, where the conditions of the dealkylation reaction are ineffective to remove the protecting group from protected norastemizole, protected norastemizole in its corresponding 3-benzimidazole acid salt form. Protected norastemizole in its corresponding 3-benzimidazole acid salt form can then be treated with base to both remove the protecting group and convert the resulting species to its free-base form, i.e., norastemizole. In such base treatment, hydroxide base is preferably used at a pH from about 9 to about 14, and most preferably from about 10 to about 12, at a temperature from about –5° C. to about 10° C., preferably at about 0° C. to about 50° C., for about 2 minutes to about 1 hour, preferably for about 2 minutes to about 30 minutes, and most preferably for about 5 minutes to about 20 minutes. Alternatively, the protecting group of protected norastemizole can be removed via acid hydrolysis, using concentrated, i.e., at least 5M, mineral acid (pH 0-1).

The norastemizole so obtained can be optionally purified by recrystallization, silica gel chromatography, high performance liquid chromatography or other methods known to those skilled in the art.

In addition, the norastemizole so obtained can be further modified, using conventional synthetic organic chemical methods, or those methods not yet known, to provide novel norastemizole analogs with more potent anti-histaminic or serotonin-agonist activities more potent than known norastemizole analogs, or with biological properties yet undiscovered.

4.2.1 SYNTHESIS OF 2-SUBSTITUTED IMIDAZOLES VIA FLUORIDE ION ACTIVATION

The 2-substituted imidazoles of the present invention can also be obtained by a process which comprises reacting, in the presence of fluoride ion, an imidazole of by formula I

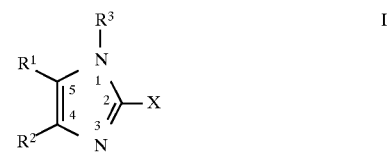

with a nucleophile to afford a 2-substituted imidazole, wherein $R^1$, $R^2$, $R^3$ and X are defined above, and wherein the nucleophile displaces X.

An example of this reaction is illustrated below in Scheme 5a:

Scheme 5a

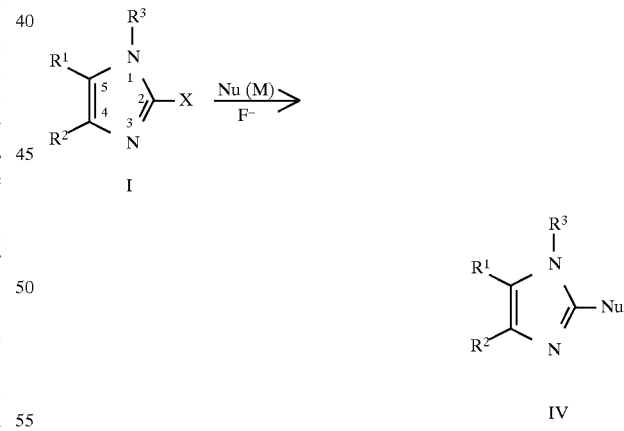

Imidazoles useful for conversion into imidazoles of formula IV are those represented by formula I, wherein $R^1$, $R^2$, $R^3$ and X are defined above. It is to be understood that the imidazole of formula I useful in this regard can be in the form of its acid salt, preferably a hydrochloride salt. Acid salts of formula I are prepared according to those methods useful for preparing imidazoles having a leaving group in the 2-position thereof as described in Section 4.1.1, above.

In a preferred embodiment, $R^3$ is 4-fluorobenzyl, $R^1$ and $R^2$ are joined together to form a benzene group, and X is a chloro group.

The imidazole of formula I is reacted, in the presence of fluoride ion, with a displacement nucleophile to afford a compound of formula IV. Suitable displacement nucleophiles include, but are not limited to, those displacement nucleophiles described in Section 4.1.1, above, except that the displacement nucleophile is not F⁻.

In one embodiment of the invention, the displacement nucleophile is ethyl 4-amino-1-piperidinecarboxylate. In another embodiment of the invention, the displacement nucleophile is 4-N-acetylaminopiperidine. In still another embodiment of the invention, the displacement nucleophile is 4-N-trimethylacetylaminopiperidine.

It will be understood that when the displacement nucleophile comprises an amino, an alkoxy, or a thioalkoxy group, the displacement nucleophile can optionally be in the form of its sodium, calcium, silver, lithium, potassium, magnesium, cerium, manganese, zinc or tin salt. Such salts are readily prepared by methods known to those skilled in the art.

The displacement nucleophile can comprise more than one "nucleophilic" groups, i.e., the displacement nucleophile can comprise more than one amino groups, more that one hydroxyl groups, more than one sulfhydryl groups, combinations of amino, hydroxyl and sulfhydryl groups, and so on. In this instance, at least one protecting group can be used to protect any other "nucleophilic" species of the displacement nucleophile that is not desired to form a bond with the 2-carbon atom of the imidazole species. Suitable protecting groups, and methods for their addition and removal, are found in Greene, supra, and can include sulfonyl groups such as optionally substituted alkyl and benzenesulfonyl groups, e.g., p-toluenesulfonyl, methanesulfonyl, trifluoromethanesulfonyl, p-methoxybenzenesulfonyl, o-nitrobenzenesulfonyl, and the like; an acid labile alkyl group such as a methoxymethyl, 2-methoxyethoxymethyl, 2-(trimethylsilyl)ethoxymethyl, 2-tetrahydropyranyl, 2-tetrahydrofuranyl, $(CH_3)_3SiCH_2CH_2$— or $Ph_3C$—; and preferably, an acyl or alkoxycarbonyl protecting group. Preferably, the protecting group is an alkoxycarbonyl or an acyl protecting group. Accordingly, a 2-substituted imidazole obtained from the reaction of the imidazole of formula I and a displacement nucleophile that has a protecting group, necessarily comprises a protecting group that resides on the portion of the displacement nucleophile that does not form a bond with the carbon atom at the 2-position of the 2-substituted imidazole.

Where the displacement nucleophile is 4-aminopiperidine, and it is desired that the primary amino group thereof form a bond with the 2-carbon of the imidazole of formula I, the protecting group for the piperidine nitrogen atom is preferably an acyl or alkoxycarbonyl protecting group. Where the protecting group is an acyl protecting group, the protecting group is preferably an acetyl or trimethylacetyl protecting group. Where the protecting group is an alkoxycarbonyl protecting group, the protecting group is preferably an ethoxycarbonyl protecting group.

Where the protecting group is an acyl protecting group, such as for example an acetyl or trimethylacetyl protecting group, the protecting group is preferably removed via acid hydrolysis using concentrated, i.e., at least 5M, mineral acid. Examples of such acid hydrolysis include treatment with 48% HBr at 100°–120° C. for 1–3h; treatment with 6N HCl at 100°–120° C. for 3–9 h; and and treatment with 12N HCl for 0.5–1 h.

Where the protecting group is an alkoxycarbonyl protecting group, such as for example an ethoxycarbonyl protecting group, the protecting group is removed via base hydrolysis, preferably at a pH from about 9 to about 14, or via acid hydrolysis, at a pH of <1.

The reaction of the imidazole of formula I with the displacement nucleophile takes place in the presence of fluoride ion. Fluoride ion can be conveniently obtained from fluoride salts which are added to the reaction mixture comprising the imidazole of formula I and the displacement nucleophile. Useful fluoride salts include, but are not limited to, tetrabutylammonium fluoride ("TBAF"), TBAF.XH₂O ("TBAF hydrate"), CsF, RbF, NaF, LiF, KF, KF/CaF₂ and mixtures thereof. If desired, up to about 5 weight % water can be added to the reaction mixture to help solvate the fluoride salts.

Optionally, the reaction of the imidazole and the displacement nucleophile, in the presence of fluoride ion, is performed in the presence of a phase transfer catalyst such as a tetraalkyl ammonium halide, e.g., trioctylmethylammonium chloride or methyltrialkyl ($C_8$–$C_{10}$) ammonium chloride. Such phase transfer catalysts are available commerically, for example, from Aldrich Chemical Co., Milwaukee, Wis. Without being bound by any particular theory, it is believed that the addition of the phase transfer catalyst can increase the overall rate of reaction between the imidazole and the displacement nucleophile.

The amount of fluoride salt, and optionally the phase transfer catalyst, used in the reaction of the imidazole of formula I with the displacement nucleophile ranges from catalytic to about 5 molar equivalents relative to the number of equivalents of the imidazole of formula I, preferably from about 0.1 to about 4 molar equivalents relative to the number of equivalents of the imidazole of formula I. In other words, when the imidazole of formula I is in an amount of 1 molar equivalent, the fluoride salt and optionally the phase transfer catalyst are each in an amount that ranges from catalytic to about 5 molar equivalents, preferably from about 0.1 to about 4 molar equivalents.

Without being bound by any particular theory, it is believed that the fluoride ion, when present in the reaction mixture comprising the imidazole of formula I and the displacement nucleophile, displaces the X group of the imidazole of formula I so as to form, in situ, an intermediate corresponding to the imidazole of formula I but where X is F. It is believed that this intermediate reacts with the nucleophile to afford the imidazole of formula IV. Furthermore, it is believed that since fluoride ion has been recognized as being a relatively poor leaving group (Francis A. Carey and Richard J. Sundberg, *Advanced Organic Chemistry* 271–72 (2d ed. 1984)), the rate limiting step of this reaction is addition of the nucleophile to the imidazole moiety, which is greatly enhanced when the X group of the imidazole of formula I is highly electron-withdrawing, e.g., F. Accordingly, the displacement nucleophile displaces the fluoride group of the intermediate to afford the imidazole of formula IV. In addition, it is believed that the reaction of the intermediate with the displacement nucleophile is an addition-elimination reaction.

The reaction of the imidazole of formula I with the nucleophile, in the presence of fluoride ion, is conducted in a polar organic solvent including, but not limited to, dimethylformamide; N-methylpyrrolidinone; tetramethylurea; dimethylimidazolone; alcohols such as methanol, ethanol, 1-propanol, 2-propanol, 1-butanol, 2-butanol and tert-butanol; and modified glycols such as $(CH_3OCH_2CH_2)_2O$, $(HOCH_2CH_2)_2O$, $CH_3OCH_2CH_2OCH_2CH_2OH$, $CH_3CH_2CH_2CH_2OCH_2CH_2OH$, $CH_3OCH_2CH_2OH$, and the like; and mixtures thereof, and at a temperature from about 80° C. to about 150° C., preferably from about 110° C. to about 130° C.

Advantageously, the reaction of the imidazole and the displacement nucleophile, in the presence of fluoride ion, is performed in the presence of a base which functions to scavenge any HF formed during the reaction. Suitable bases useful in this regard include, but are not limited to, pyridine, collidine, lutidine, diisopropylethylamine, methyl di-tertbutylamine, tributylamine, and other high boiling organic amines. Preferably, base is an organic amine, most preferably, lutidine. Optionally, following the reaction between the imidazole and the displacement nucleophile, additional base, preferably in the form of aqueous sodium hydroxide, can be added to the reaction mixture if desired.

In a preferred embodiment of the invention, $R^1$ and $R^2$ are joined together to form a benzene group, $R^3$ is 4-fluorobenzyl, and the X group of the imidazole of formula I is Cl.

The course of the reaction between the imidazole of formula I and the displacement nucleophile, in the presence of fluoride ion, can be measured spectroscopically, using, for example, HPLC. The imidazole of formula IV can optionally be purified by recrystallization, column chromatography, or other methods known to those skilled in the art.

In an alternate embodiment of the invention, prior to reaction of the imidazole of formula I with the displacement nucleophile (in the presence of fluoride ion), the imidazole of formula I can be selectively alkoxycarbonylated or sulfonylated at the 1-position so as to afford, following reaction with the displacement nucleophile in the presence of fluoride ion, a 1-N-alkoxycarbonyl- or 1-N-sulfonyl-2-substituted imidazole of formula IV. It will be understood that in this case, the imidazole of formula I used in the alkoxycarbonylation or sulfonylation reaction is unsubstituted at the 1-position, i.e., where $R^3$ is H. The combination of using fluoride ion and alkoxycarbonylating or sulfonylating the 1-position of the imidazole of formula I is "doubly activating" in that in addition to bearing a 2-fluoro group as a reactive intermediate, the imidazole moiety also bears a 1-N-alkoxycarbonyl or -sulfonyl group which withdraws electron density therefrom, thereby further increasing its electrophilicity at the 2-position. Accordingly, the presence of the 1-N-alkoxycarbonyl or -sulfonyl group accelerates the rate of reaction between the 1-N-alkoxycarbonylated or 1-N-sulfonylated imidazole species of formula I and the displacement nucleophile.

Preferably, the displacement nucleophile is a 1-N-protected 4-aminopiperidine. Most preferably, the displacement nucleophile is an acyl- or alkoxycarboxyl-protected 4-amino piperidine described above.

Following reaction of the displacement nucleophile with the 1-N-alkoxycarbonylated or 1-N-sulfonylated imidazole of formula I, the 1-N-alkoxycarbonyl or -sulfonyl group is removed. If the displacement nucleophile has a protecting group that is not removable under conditions used to remove the 1-N-alkoxycarbonyl or -sulfonyl group, the 1-N-alkoxycarbonyl or -sulfonyl group can be removed in a subsequent step.

Useful alkoxycarbonyl groups are typically $C_1$–$C_6$ alkoxycarbonyl groups. Preferably, the $C_1$–$C_6$ alkoxycarbonyl group is a tert-butoxycarbonyl group. Useful sulfonyl groups are optionally substituted alkyl- and benzenesulfonyl groups, such as for example, p-toluenesulfonyl, methanesulfonyl, trifluoromethanesulfonyl, p-methoxybenzenesulfonyl, o-nitrobenzenesulfonyl, and the like. Typically, sulfonylation can occur via treatment with a sulfonyl halide, preferably in the presence of base, such as for example a metal carbonate or bicarbonate, or an organic amine. Methods of addition and removal of alkoxycarbonyl and sulfonyl groups are well known in the art. Examples of addition and removal of alkoxycarbonyl and sulfonyl groups can be found in Greene, supra. When the sulfonyl group is a p-toluenesulfonyl group, the sulfonyl group is preferably removed with a mixture of 2 eq. of $HSCH_2CO_2H$ and excess LiOH, most preferably in dimethyl formamide solvent, and at temperature of about 0° C. to about 80° C., preferably about 20° C. to about 60° C., for about 2 minutes to about 15 minutes, preferably for about 5 to about 10 minutes.

Following removal of the alkoxycarbonyl or a sulfonyl group, the 1-position of the imidazole of formula IV moiety can be functionalized, preferably alkylated via conventional alkylation techniques. In a preferred embodiment, the 1-position of the imidazole of formula IV is alkylated with a benzyl halide, preferably 4-fluorobenzyl bromide. In the preferred embodiment, the benzylation reaction is performed in the presence of excess base, preferably a metal hydroxide and most preferably, potassium hydroxide. In addition, the benzylation reaction preferably is performed in a polar organic solvent, preferably dimethylformamide, at a temperature of about room temperature to about 100° C., preferably from about 40° C. to about 60° C., for about 5 minutes to about 6 hours, preferably from about 10 minutes to about 1 hour, and most preferably from about 10 minutes to about 30 minutes.

If the displacement nucleophile has a protecting group that is not removed under the conditions used in any of the above transformations, such a protecting group can be removed by the methods described above.

In a further embodiment of the invention, the imidazole of formula I is treated with an alkylating agent as described above in Section 4.1.1 and then alkoxycarbonylated or sulfonylated, or vice versa, so as to obtain an imidazole of formula II wherein $R^3$ is an alkoxycarbonyl or a sulfonyl group. It will be understood that in this embodiment, the imidazole of formula I that is treated with an alkylating agent and then alkoxycarbonylated or sulfonylated, or vice versa, is unsubstituted at the 1-N position, i.e., where $R^3$ is H. The imidazole of formula II that has an alkoxycarbonyl or a sulfonyl group at $R^3$ is then treated with a displacement nucleophile, optionally in the presence of fluoride ion as described above, and subsequently dealkylated to afford the imidazole of formula IV. Preferably, the alkoxycarbonyl or sulfonyl group is removed during the dealkylation step. If the conditions used in the dealkylation step are ineffective to remove the alkoxycarbonyl or sulfonyl group, a subsequent step to remove the alkoxycarbonyl or sulfonyl group may be required. Conditions useful for removing alkoxycarbonyl or sulfonyl group are described above. If the alkoxycarbonyl or sulfonyl group is removed from the 1-N-position of the imidazole of formula IV, the resulting unsubstituted 1-nitrogen atom can be alkylated, preferably benzylated and most preferably 4-fluorobenzylated, as described above.

4.2.2 SYNTHESIS OF NORASTEMIZOLE VIA FLUORIDE ION ACTIVATION

The present invention encompasses a method for synthesizing norastemizole via fluoride ion activation. This method is illustrated below in Scheme 5b:

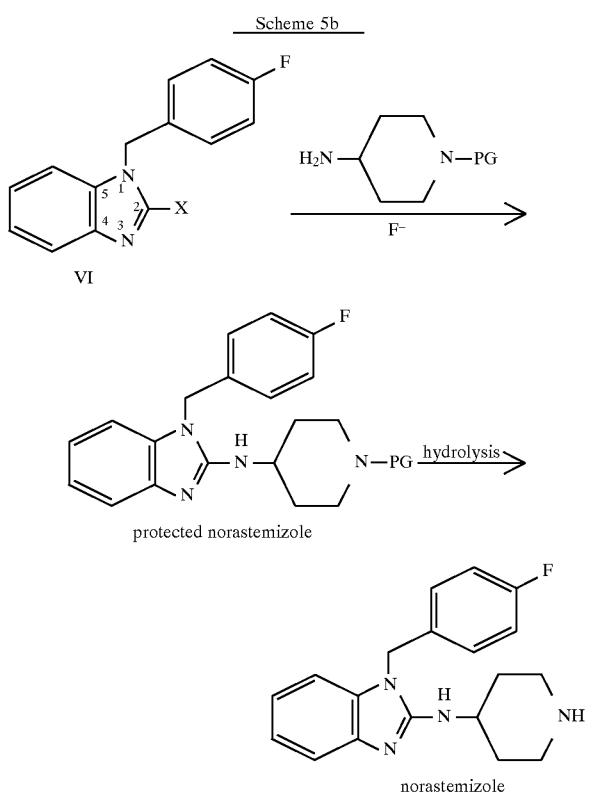

Scheme 5b protected norastemizole norastemizole

In the first step, the benzimidazole of formula VI, wherein X is defined as above, is reacted, in the presence of fluoride ion, with a displacement nucleophile that is a 1-N-protected 4-aminopiperidine. The reaction of the benzimidazole of formula VI with the N-protected 4-aminopiperidine affords protected norastemizole. It will be understood that the benzimidazole of formula VI is a 1-(4-fluorophenylmethyl) -1H-benzimidazole having a leaving group, X, in the 2-position. In a preferred embodiment of the invention, the X group of the benzimidazole of formula VI is a Cl group, such that the 1-(4-fluorophenylmethyl)-1H-benzimidazole having a leaving group in the 2-position is 2-chloro-1-(4-fluorophenylmethyl)-1H-benzimidazole.

Protecting groups suitable for the N-protected 4-aminopiperidine displacement nucleophile can be found in Greene, supra, and can include sulfonyl groups such as optionally substituted alkyl and benzenesulfonyl groups, e.g., p-toluenesulfonyl, methanesulfonyl, trifluoromethanesulfonyl, p-methoxybenzenesulfonyl, o-nitrobenzenesulfonyl, and the like; an acid labile alkyl group such as a methoxymethyl, 2-methoxyethoxymethyl, 2-(trimethylsilyl)ethoxymethyl, 2-tetrahydropyranyl, 2-tetrahydrofuranyl, $(CH_3)_3SiCH_2CH_2$— or $Ph_3C$—; and preferably, an acyl or alkoxycarbonyl protecting group. In one embodiment of the invention, the protecting group for the N-protected 4-aminopiperidine is an alkoxycarbonyl protecting group, such as one described above, and in particular, an ethoxycarbonyl protecting group. In another embodiment of the invention, the protecting group for the N-protected 4-aminopiperidine is an acyl protecting group and in particular, an acetyl or a trimethylacetyl protecting group.

Where the protecting group is an ethoxycarbonyl protecting group, the displacement nucleophile is ethyl 4-amino-1-piperidinecarboxylate. Where the protecting group is an acetyl protecting group, the displacement nucleophile is 4-N-acetylaminopiperidine. Where the protecting group is a trimethylacetyl protecting group, the displacement nucleophile is 4-N-trimethylacetylaminopiperidine.

Because the N-protected 4-aminopiperidine displacement nucleophile is an amino nucleophile, i.e., the 4-amino group of the N-protected 4-aminopiperidine displaces the X group of the benzimidazole of formula VI, the 4-amino group of the displacement nucleophile can optionally be in the form of a salt as described in Section 4.2.1, above.

The reaction of the benzimidazole of formula VI with the N-protected 4-aminopiperidine displacement nucleophile takes place in the presence of fluoride ion. Fluoride ion can be conveniently obtained from fluoride salts which are added to the reaction mixture comprising the benzimidazole of formula VI and the N-protected 4-aminopiperidine. Useful fluoride salts include, but are not limited to, those described in Section 4.2.1, above.

The amount of fluoride salt, and optionally the phase transfer catalyst, used in the reaction of the imidazole of formula VI with the displacement nucleophile ranges from catalytic to about 5 molar equivalents relative to the number of equivalents of the imidazole of formula VI, preferably from about 0.1 to about 4 molar equivalents relative to the number of equivalents of the imidazole of formula VI. In other words, when the imidazole of formula VI is in an amount of 1 molar equivalent, the fluoride salt and optionally the phase transfer catalyst are each in an amount that ranges from catalytic to about 5 molar equivalents, preferably from about 0.1 to about 4 molar equivalents.

Depending upon the choice of solvent, and whether or not a base is employed, the reaction between the benzimidazole of formula VI and the N-protected 4-aminopiperidine can be >75% complete within several hours.

The second step of the process involves removing the protecting group from protected norastemizole to obtain norastemizole. Methods for removing various protecting groups of an amino group can be found in Greene, supra.

Where the protecting group is an acyl protecting group, for example an acetyl or trimethylacetyl protecting group, the protecting group is preferably removed via acid hydrolysis using concentrated, i.e., at least 5M, mineral acid. In a preferred embodiment, the acid used to remove the acetyl group is 6N hydrochloric acid, and the acid used to remove the trimethylacetyl protecting group is 12N hydrochloric acid. Removal of an acyl protecting group typically proceeds at a temperature of about 80° C. to about 140° C., preferably from about 100° C. to about 120° C., and most preferably at about 110° C., and for about 0.5 to about 8 hours, preferably from about 1 to about 6 hours. It is to be pointed out that where the protecting group is an acetyl group, the acetyl group can optionally be removed using aqueous base, preferably NaOH, at a pH of $\geq 3$.

It will be understood that where an acid hydrolysis is used to remove a protecting group from protected norastemizole, the resulting norastemizole product will be in the form of its acid salt, corresponding to the acid used in the acid hydrolysis. The acid salt of norastemizole can them be converted to its free base by treatment with concentrated aqueous base, preferably 50% NaOH at 0°–50° C., or by any other methods known to those skilled in the art.

Where the protecting group is an alkoxycarbonyl protecting group, such as for example an ethoxycarbonyl protecting group, the protecting group is can be removed via acid hydrolysis as described above, preferably with 48% hydrobromic acid. Alternatively, the alkoxycarbonyl group can be removed via base hydrolysis, preferably at a pH from about 9 to about 14, and most preferably at a pH of >12, e.g., using 6–12N NaOH. Such base hydrolysis can typically occur using concentrated aqueous base, preferably 50% NaOH, optionally in the presence of a water soluble organic solvent such as ethanol, at about 75° C. to about 85° C., for about 5 to about 30 hours.

4.3 METHODS FOR USE OF 2-SUBSTITUTED IMIDAZOLES

The use of certain novel 2-substituted imidazoles of the present invention, pharmaceutically acceptable salts thereof, and enantiomeric forms of the 2-substituted imidazoles in compositions of the present invention is based on their useful pharmacological properties. More particularly, they are active as anti-histaminics. In addition thereto, they are also devoid of sedating effects which is an undesirable side-effect often encountered with anti-histaminics. Apart from their anti-histaminic properties they also show serotonin-antagonism.

Furthermore, the 2-substituted imidazoles, in particular norastemizole, are particularly attractive due totheir favorable pharmacokinetic profile. On the one hand they show a rapid onset so that their anti-histaminic effects are almost instantaneously present. On the other hand they possess an attractive duration of effect, i.e., while being not too short, thus avoiding the necessity of frequent administrations, said duration is not too long either. Hence, the dose regimen can suitably be adapted to the evolution of the symptoms.

To prepare pharmaceutical compositions of this invention, an effective amount of the particular 2-substituted imidazole, preferably a pharmaceutically acceptable salt thereof, as the active ingredient is combined in intimate admixture with a pharmaceutically acceptable carrier, which carrier may take a wide variety of forms depending on the form of preparation desired for administration. These pharmaceutical compositions are desirably in unitary dosage form, suitable for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parental compositions, the carrier will usually comprise sterile water, at least in large part, though other ingredients, for example, to aid solubility, may be included. Injectable solutions, for example, may be prepared in which the carrier comprises saline solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Pharmaceutically acceptable salts of the present 2-substituted imidazoles, due to their increased water solubility over the corresponding free-base form, are obviously more suitable in the preparation of aqueous compositions It is especially advantageous to formulate the aforementioned pharmaceutical compositions in dosage unit form for each of administration and uniformity of dosage. "Dosage unit form" refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiple thereof.

The 2-substituted imidazoles are preferably administered as pharmaceutically acceptable salts thereof. Examples of such pharmaceutically acceptable salts include, but are not limited to, hydrochloride, hydrobromide, hydroiodide, sulfate, hydrogensulfate, phosphate, hydrogenphosphate, dihydrogenphosphate, succinate, ascorbate, tartrate, citrate, gluconate, benzoate, malate, malonate, fumarate, acetate, sulfuric acid salts, $Mg^{2+}$, $Zn^{2+}$, and the like.

In a further aspect of the present invention there is provided a method of treating allergic diseases in warm-blooded animals suffering from said allergic diseases, which method comprises the administration to said warm-blooded animals of an effective anti-allergic amount of a 2-substituted imidazole of the present invention. Preferably said effective amount of the active ingredient is administered as a composition as described hereinabove. It is within the purview of one of skill in the art to determine the optimal effective anti-allergic amount of the active ingredient. In general it is contemplated that an effective amount would be from about 0.001 mg/kg to about 100 mg/kg body weight, and more preferably from about 0.01 mg/kg to about 1 mg/kg body weight.

The present invention is versatile and can be used to prepare novel 2-substituted imidazoles having biological activity, in particular, anti-histaminic and serotonin-antagonism properties, that are superior to those of known 2-substituted imidazoles. Biological activities of the novel 2-substituted imidazoles obtainable via the methods of the present invention can be assessed using the ($^3$H)pyrilamine binding assay as described in Chang et al., *J. Neurochem.* 32:1653–1663 (1979).

The following series of Examples relate to the synthesis of norastemizole, some of which are illustrated schematically in Schemes 6–9, below. These Examples are presented by way of illustration and not by way of limitation on the scope of the invention.

5. EXAMPLE: SYNTHESIS OF NORASTEMIZOLE

High-performance liquid chromatography (HPLC) materials and methods: Column, µBondapak C-18, 10 µm, 30 cm×3.9 mm; detection, 220 nm; mobile phase, 0.1M $NaClO_4$/0.01M $NaH_2PO_4$:acetonitrile (50:50); flow, 1.0 mL/min. 2-chloro-1-(4-fluorophenylmethyl)-1H-benzimidazole (Compound X) was obtained commercially as its hydrochloride salt from Lancaster Synthesis Inc., Windham, N.H. Compound X was used either as its commercially available hydrochloride salt, or in its free base form. Conversion of the hydrochloride salt of Compound X to its free base form was accomplished by methods known to those of ordinary skill in the art.

The following Examples 1–7 relate to a synthesis of norastemizole via a 3-N alkyl imidazolium species (Schemes 6 and 7), and intermediates useful therefor.

EXAMPLE 1

Compound XI. To a 500 mL, 3-neck flask equipped with a thermometer and stirring bar were added 13.0 g (50 mmol, 1.0 eq.) of 2-chloro-1-(4-fluorophenylmethyl)-1H-benzimidazole (X) (Lancaster Synthesis Inc., Windham, N.H.) and 200 mL of anhydrous toluene under a $N_2$ atmosphere. 7.35 mL (1.8 eq.) of methoxymethyl bromide were added to the reaction mixture over 2–3 minutes at 20°–25° C. The resulting mixture was allowed to stir at 25° C. for 1 hour, whereupon a white slurry formed. The progress of the reaction was monitored using high performance liquid chromatography. Compound XI was collected by vacuum filtration of the reaction mixture, washed with toluene (2×20 mL) and was used as a wet cake in the next step without further purification.

EXAMPLE 2

Compound XIII. The wet cake of Compound XI, obtained according to the procedure of Example 1, was transferred to a 500 mL, 3-neck flask without further drying. 200 mL of anhydrous toluene were added, with stirring, followed by slow addition of 10.67 mL (62 mmol, 1.34 eq.) of ethyl 4-amino-1-piperidine carboxylate (XII) (Lancaster Synthesis Inc., Windham, N.H.) at room temperature. The resulting mixture was allowed to warm to 50° C., and stir at this temperature for 2–3 hours. The progress of the reaction was monitored using high performance liquid chromatography. The resulting solid product was isolated using vacuum filtration, and was washed with toluene (2×20 mL). The resulting wet cake was dried at 25°–30° C./5–10 mm/Hg for 10–14 hours, affording 22.7 g of Compound XIII. Compound XIII can be stored at ambient temperature for at least two months without appreciable decomposition.

EXAMPLE 3

Norastemizole. To a 100 mL, 3-neck flask equipped with a thermometer, a reflux condenser and a stirring bar were added 6.0 g (10.8 mmol, 1.0 eq.) of Compound XIII, obtained according to the procedure of Example 2, and 20 mL of anhydrous methylene chloride, under a $N_2$ atmosphere. The resulting mixture was allowed to stir at 20°–25° C. for 5 minutes, forming a suspension, and then was allowed to cool to 0°–5° C. 3.0 mL (32.4 mmol, 3.0 eq.) of boron tribromide was added dropwise to the reaction mixture with cooling (<30° C.). Following the addition of boron tribromide, the resulting mixture was allowed to stir at 20°–25° C. for 10–20 minutes. The reaction mixture was allowed to cool to 0°–5° C., whereupon 40 mL of MeOH were added slowly at <40° C over 10–20 minutes. The resulting solution was concentrated in vacuo, at 30°–50° C., to a total volume of approximately 20 mL. 60 mL of tert-butylmethyl ether ("TBME") were added, and the resulting suspension was allowed to cool to 0°–5° C., and stir at that temperature for 1 hour. The progress of the reaction was monitored using high performance liquid chromatography. The resulting solid was collected by vacuum filtration, washed with TBME, and dried at 40° C./10–20 mm/Hg for 2 hours.

The dry, solid obtained above was transferred to a 50 mL, 3-neck flask, whereupon 10 mL of 48% hydrobromic acid were added. The resulting mixture was heated to 110° C. for 1 hour, with stirring. The progress of the reaction was monitored using thin layer chromatography and high performance liquid chromatography. After the reaction was complete, the reaction mixture was allowed to cool to room temperature, affording a solution comprising Compound XIVb.

The solution comprising Compound XIVb was diluted with 10 mL of toluene and 20 mL of water, with stirring. The resulting mixture was allowed to cool to 0°–5° C., and to it was slowly added 50% aqueous NaOH until the pH of the resulting mixture was >11. The resulting slurry was allowed to stir at 0°–5° C. for 1 hour, and was then vacuum filtered. The resulting wet cake was washed thoroughly with water (2×10 mL), and dried on the vacuum funnel, under vacuum, for 30 minutes. The resulting crude product was mixed with 6 mL of ethyl acetate and heated to reflux. 40 mL of TBME was added under gentle reflux (50°–60° C.) with stirring. The resulting suspension was allowed to cool to 0°–5° C., and was allowed to stir at that temperature for 1 hour. The resulting mixture was filtered, and the resulting wet cake was washed with TBME, and dried at 25° C./5–10 mm/Hg for 5 hours to afford 2.02 g of norastemizole in 46% overall yield from Compound X: $^1$H NMR (300 MHz, DMSO-$d_6$) δ7.23–7.17 (4H, m), 7.04 (1H, m), 6.91 (1H, m), 6.83 (1H, m), 6.63 (1H, m), 3.80 (1H, m), 2.96 (2H, m), 2.52 (2H, m), 1.92 (2H, m), 1.38 (2H, m); $^{13}$C NMR (75 MHz, DMSO-$d_6$) δ162.7, 160.0, 153.9, 142.9, 134.3, 133.4, 129.0, 128.9, 120.5, 118.3, 115.4, 115.2, 114.9, 107.74, 50.7, 45.5, 43.6, 33.6.

EXAMPLE 4

Norastemizole. To a 50 mL, 3-neck flask equipped with a thermometer, a reflux condenser and a stirring bar were added 3.0 g (5.4 mmol, 1.0 eq.) of Compound XIII, obtained according to the procedure of Example 2, and 10 mL of anhydrous methylene chloride, under a $N_2$ atmosphere. The resulting mixture was allowed to stir at 20°–25° C. for 5 minutes, forming a suspension, and then was allowed to cool to 0°–5° C. using an ice-water bath. 1.5 mL (16.2 mmol, 3.0 eq.) of boron tribromide was added dropwise to the reaction mixture with cooling (<300 C). Following the addition of boron tribromide, the resulting mixture was allowed to stir at 20°– 25° C. for 10–20 minutes. The reaction mixture was allowed to cool to 0°–5° C., whereupon 20 mL of 25% aqueous hydrochloric acid were slowly added. The resulting mixture was heated to 110° C. for 2 hours, with stirring. The progress of the reaction was monitored using high performance liquid chromatography. After cooling to room temperature, the resulting mixture was diluted, sequentially, with 5 mL of toluene and 10 mL of water, with stirring. The resulting mixture was allowed to cool to 0°–5° C., and to it was slowly added 50% aqueous NaOH until the pH of the resulting mixture was >11. The resulting slurry was allowed to stir at 0°–5° C. for 1 hour, and was then vacuum filtered. The resulting wet cake was washed thoroughly with water (2×5 mL), and dried on the vacuum funnel, under vacuum, for 30 minutes. The resulting crude product was mixed with 3 mL of ethyl acetate and heated to reflux. 20 mL of TBME was added under gentle reflux (50°–60° C.) with stirring. The resulting suspension was allowed to cool to 0°–5° C., and was allowed to stir at that temperature for 1 hour. The resulting mixture was filtered, and the resulting wet cake was washed with TBME, and dried at 25° C./5–10 mm/Hg for 5 hours to afford 1.07 g of norastemizole in 50% overall yield from Compound X.

EXAMPLE 5

Norastemizole. To a 25 mL, 3-neck flask equipped with a thermometer, a reflux condenser and a stirring bar were added 0.600 g (1.07 mmol, 1.0 eq.) of Compound XIII, obtained according to the procedure of Example 2, 2 mL of pyridine and catalytic 4-dimethylaminopyridine, under a $N_2$ atmosphere. The resulting mixture was heated to 70°–90° C. for 6 hours, with stirring. The progress of the reaction was monitored using high performance liquid chromatography. The resulting mixture was diluted with a solution formed from 2 ml of 5N NaOH and 6 mL of EtOH, at heated at reflux for 18–24 h. The progress of the reaction was monitored using high performance liquid chromatography. The reaction mixture was concentrated in vacuo (30°–45° C./80–100 mm/Hg) to a volume of approximately 3 mL. The resulting concentrate was diluted with 10 mL of toluene, and the resulting mixture was once again concentrated to a volume of approximately 5 mL. To the resulting slurry was added 2 mL of 10% $Na_2CO_3$ solution, and the resulting mixture was cooled to 0°–5° C. and allowed to stir for 2–3 h. The resulting solid product was vacuum filtered and washed with toluene (2×2 mL). The solid product was then mixed with 5 mL of toluene, and the resulting mixture was heated at 70°–80° C. for 5 minutes. The mixture was cooled to 0°–5° C., and was allowed to stir at that temperature for 2 h. The resulting crystalline product was filtered, washed with toluene, and dried at 40°–45° C. for 4 h to afford 0.242 g of norastemizole in 56% overall yield from Compound X.

EXAMPLE 6

Compound XVI. 23.5 g (167 mmol) of 1-acetyl-4-piperidone (Aldrich Chemical Co., Milwaukee, Wis.) and 12.5 g (179 mol) of hydroxylamine hydrochloride were placed in a 250 mL flask with 200 mL of methanol. To the resulting mixture was added 19.0 g (180 mmol) of sodium carbonate, and the resulting mixture was allowed to stir at room temperature for 12–14 h. The reaction mixture was concentrated in vacuo to afford 23.5 g of 1-acetyl-4-hydroxyiminopiperidine as a white solid: $^1H$ NMR (300 MHz, $CDCl_3$) δ3.72 (dd, 2H, J=11.0, 6.0 Hz), 3.59 (ddd, 2H, J=13.8, 6.2, 6.2 Hz), 2.68 (ddd, 2H, J=10.6, 6.2, 6.2 Hz), 2.42 (ddd, 2H, J=12.2, 6.1, 6.1 Hz), 2.17 (d, 3H, J=3.9 Hz); $^{13}C$ NMR (75 MHz, $CDCl_3$) δ169.39, 169.29, 156.07, 155.78, 45.95, 44.31, 41.68, 39.65, 31.27, 30.46, 25.04, 24.42, 21.47, 21.44.

23.5 g of the 1-acetyl-4-hydroxyiminopiperidine obtained above was placed into a reaction vessel and to it was added 200 mL of methanol containing 40 mL of $CHCl_3$. 2.0 g of $PtO_2$ was added to the reaction vessel, and the reaction vessel was placed under 50 psi of $H_2$ and shaken at room temperature for 24 h. The resulting reaction mixture was filtered and the filtrate was concentrated to afford 21 g (71%) of Compound XVI, in the form of its hydrochloride salt, as a white solid. The solid was recrystallized from a minimum of hot ethanol to yield a white, crystalline solid: Hydrochloride salt $^1H$ NMR (300 MHz, $D_2O$) δ4.36 (d, 1H, J=13 Hz), 3.93 (d, 1H, J=13 Hz), 3.41 (m, 1H), 3.14 (m, 1H), 2.70 (m, 1H), 2.03 (s, 3H), 2.01 (m, 2H), 1.5 (m, 2H); $^{13}C$ NMR (75 MHz, $D_2O$) δ172.08, 47.75, 44.51, 39.86, 29.38, 28.82, 20.28.

EXAMPLE 7

Norastemizole was obtained according to the procedures of Examples 1, 2 and 5 above, except that 2-methoxyethoxymethyl chloride was used in place of methoxymethyl bromide, Compound XVI was used in Compound XII, and 4-dimethylaminopyridine was used in place of pyridine.

It is to be pointed out that Compound XVI reacts with Compound X (118° C., 36–45 h, n-butanol solvent) to form Compound XVIII in 70–80% yield, which can be deprotected as described above to afford norastemizole. However, in addition to Compound XVIII, 30–40% of undesired regioisomer Compound XIX is formed, which is extremely difficult to purify from Compound XVIII.

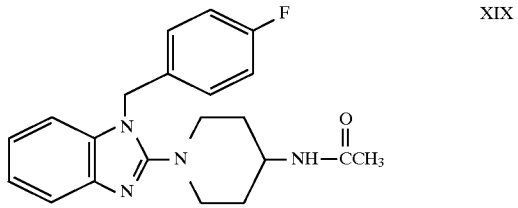

Surprisingly, during the reaction of benzimidazolim Compound XV with Compound XVI at 40°–60° C. for 3–4 h, less than 5% of undesired regioisomer Compound XX is formed.

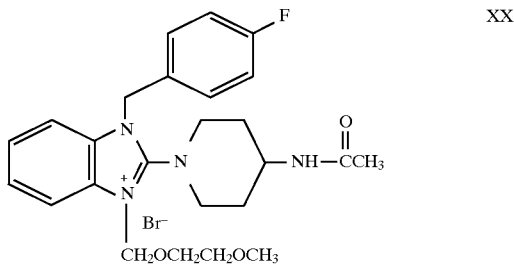

Because of its 3-N alkyl group, Compound XV is activated relative Compound X, and can accordingly react to form a stable adduct with Compound XVI under milder conditions than those required in the reaction of Compound X with Compound XVI. Without being bound by any particular theory, it is believed that the reaction between Compound XV and Compound XVI, by virtue of the fact that a lower reaction temperature and much shorter reaction time can be employed, gives rise to a substantially smaller amount of undesired regioisomer. Compound XVII, the desired product of the reaction between Compound XV and Compound XVI, is dealkylated and subsequently deprotected to provide norastemizole. Accordingly, Compound XVII, as well as compounds of formula XXI, where $R^4$ and $Y^-$ are defined above, have utility as intermediates for norastemizole, wherein the compounds of formula XXI are obtained in high yield with minimal accompanying formation of undesired regioisomers.

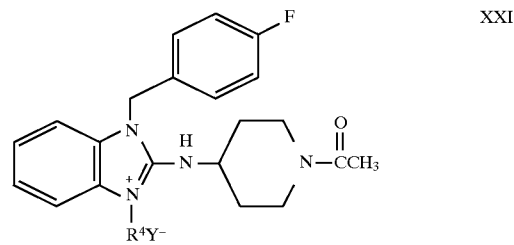

The following Examples 8a and 8b relate to syntheses of Norastemizole via fluoride ion activation.

EXAMPLE 8a

To a 25 mL 3-neck flask equipped with a thermometer, reflux consenser and stir bar were added, under a nitrogen atmosphere, 822 mg (4.8 mmol) of Compound XII (Lancaster Synthesis, Inc., Windham, N.H.), and 0.93 mL of lutidine. The mixture was heated to 120° C., whereupon a solution of 1.04 g (4 mmol., 1 eq.) of Compound X (Aldrich Chemical Co., Milwaukee, Wis.), 8 mmol of tetrabutylammonium fluoride (obtained from its 1.0M THF solution by distillation under vacuum with anhydrous toluene) and 4 mL of N-methylpyrrolidinone was added slowly over 2 h. The reaction mixture was allowed to stir at 120° C. for 1 h. High-performance liquid chromatography revealed >95% coversion to Compound XIVa (in free base form). The reaction mixture was allowed to cool to ambient temperature, and slowly poured into a solution of 5% aqueous NaOH while stirring. The resulting suspension was allowed to stir at 0°–10° C. for 30 minutes, and the resulting solid product was collected by vacuum filtration, washed with water (3×5 mL), and air dried for 30 minutes under vacuum to afford crude Compound XIVa (in free base form): $^1$H NMR (300 MHz, CDCl$_3$) δ7.53 (1H, d, J=7.8 Hz), 7.22–6.92 (7H, m, two groups), 5.12 (2H, s), 4.37 (1H, NH br. d), 4.12 (2H+1H, m overlapped), 4.07 (2H, q, J=7.0 Hz), 2.98 (2H, pseudo t), 2.09 (2H, pseudo d), 1.30 (2H, m overlapped), 1.24 (3H, t, J=7.0 Hz); $^{13}$C NMR (75 MHz, CDCl$_3$) δ164.2 and 161.0 ($^{13}$C-$^{19}$F coupling), 155.6, 153.3, 142.2, 134.5, 131.4, 128.3, 121.8, 120.0, 116.6, 116.3, 116.1, 107.5, 61.5, 50.1, 45.0, 42.8, 32.6, 14.8. It is to be noted that under the same reaction conditions as above, but without the use of tetrabutylammonium fluoride, only 5% conversion (high-performance liquid chromatography) to Compound XIVa (in free base form) was achieved after 3 h at 120° C.

The crude Compound XIVa (in free base form) obtained above was placed in a 50 mL, 3-neck flask equipped with a thermometer, reflux condenser and stir bar. 5 mL of 48% hydrobromic acid was added, and the resulting mixture was heated to 110° C. and allowed to stir at that temperature for 2 h. After the reaction was complete (>98% conversion to norastemizole as shown by high-performance liquid chromatography), the reaction mixture was allowed to cool to room temperature, and 10 mL of toluene and 10 mL of water were added, with stirring. The resulting mixture was allowed to cool to 0°–5° C., and 50% aqueous NaOH was slowly added until the pH of the mixture was >11. The resulting slurry was allowed to stir at ambient temperature for 1 hour, and was then filtered under vacuum. The resulting wet cake was 25 thoroughly washed with water (3×5 mL) and toluene (2×5 mL), and was air dried for 30 minutes. The resulting wet material was further dried at 25° C./5–10 mm Hg for 6–10 hours to afford 0.91 g of norastemizole in 70% overall yield from Compound X. The structure of norastemizole was confirmed by $^1$H NMR.

EXAMPLE 8b

To a 500 mL 3-neck flask equipped with a thermometer, reflux consenser, overhead stirrer and addition funnel were added, under a nitrogen atmosphere, 23.8 g (80 mmol) of Compound X (Aldrich Chemical Co., Milwaukee, Wis.), and 32 mL of CH$_3$OCH$_2$CH$_2$OCH$_2$CH$_2$OH. To the resulting mixture was added 11.2 mL of lutidine, whereupon the temperature of the reaction mixture rose to 40°–45° C. The resulting mixture was allowed to stir at 30°–45° C. for 10–15 minutes. 16.4 g (96 mmol) of Compound XII (Lancaster Synthesis, Inc., Windham, N.H.) was added over 2–3 minutes. After allowing the resulting reaction mixture to stir at 30°–40° C. for 10 minutes, 0.85 mL (1 weight %) of water, followed by 1.39 g (24.0 mmol) of KF were added. The reaction mixture was heated to 124°–127° C. over 30 minutes (at this point, >98% conversion to protected norastemizole as shown by high-performance liquid chromatography), and the reaction mixture continued to heat at this temperature until conversion was complete. The reaction mixture was allowed to cool to 50°–60° C., and was diluted with 80 mL of toluene. 200 g of a 4% aqueous NaOH solution was added, and the resulting mixture was allowed to stir at 30°–40° C. for 10–15 minutes. The reaction mixture was allowed to cool to 0°–5° C., and was allowed to stir at that temperature for 2–3 h. The resulting solid product was collected by vacuum filtration, washed with water (3×20 mL), and air dried for 30 minutes under vacuum to afford crude Compound XIVa in free base form, (chemical purity 98.9%) having $^1$H and $^{13}$C NMR data consistent with that obtained for Compound XIVA in Example 8a, above.

63.7 g of wet, crude Compound XIVa (in free base form) obtained above, and 264 mL of ethanol, were placed in a 1 L, 3-neck flask equipped with a thermometer, reflux condenser, overhead stirrer and addition funnel. To the resulting slurry was added a solution of NaOH (50 g in 66 mL of water) under an atmosphere of N$_2$. The reaction mixture was heated at reflux for 14 h (>99% conversion to norastemizole as shown by high-performance liquid chromatography). After cooling to room temperature, the reaction mixture was diluted with 150 mL of ethanol, and filtered. The resulting filtrate was concentrated by distillation to approximately half of the filtrate volume, and diluted with water (370 mL). The resulting mixture was further distilled until the temperature of the distillate reached 100° C. (760 mm/Hg). The remaining slurry was allowed to cool to 0°–5° C., and was allowed to stir for 2 h. The white to off-white crystalline residue was collected by vacuum filtration, washed with water (5×100 mL), and dried at 50°–60° C. at 5–10 mm/Hg for 10–12 h to afford 39.7 g (87%) of pure norastemizole. The structure of norastemizole was confirmed by $^1$H NMR.

The following Examples 9–15 relate to the reaction of Compound X with Compound XII in the presence of tetrabutylammonium fluoride (dried from 1.0M THF solution).

EXAMPLES 9–15

Following the procedure of Example 8a, above, but with some reagent substitutions shown below, Compound X and Compound XII were coupled in the presence of tetrabutylammonium fluoride (dried from 1.0M THF solution). In Example 14, no fluoride ion was used. The results are shown below in Table 1:

TABLE 1

| Example | F$^-$ | F$^-$: Compound X Ratio | Solvent | Base | Conditions | % Conversion (HPLC) |
|---|---|---|---|---|---|---|
| 9 | TBAF | 2:1 | DMF | — | 120° C./1.5 h | 86.8 |
| 10 | TBAF | 2:1 | NMP | — | 120° C./2 h | 75 |
| 11 | TBAF | 2:1 | TMU | — | 120° C./2 h | 69 |
| 12 | TBAF | 2:1 | DMI | — | 120° C./2 h | 69.5 |
| 13 | TBAF | 2:1 | NMP | lutidine (1 eq.) | 120° C./1 h | 68.8 |

TABLE 1-continued

| Example | F⁻ | F⁻:Compound X Ratio | Solvent | Base | Conditions | % Conversion (HPLC) |
|---|---|---|---|---|---|---|
| 14 | — | — | NMP | lutidine (1 eq.) | 120° C./6 h | 8.1 |
| 15 | TBAF | 2:1 | NMP | — | 120° C./1 h | 72.5 |

TBAF = tetrabutylammonium fluoride (dried from THF solution)
THF = tetrahydrofuran
DMF = dimethylformamide
NMP = N-methylpyrrolidinone
TMU = tetramethylurea
DMI = dimethylimidazolone As can be seen in Table 1, the rate of reaction between Compound X and Compound XII when fluoride ion is present, relative when fluoride ion is absent (Example 14), was dramatically enhanced.

The following Examples 16–24 relate to the reaction of Compound X with Compound XII in the presence of tetrabutylammonium fluoride hydrate.

EXAMPLES 16–24

Following the procedure of Example 8a, above, but with some reagent substitutions shown below, Compound X and Compound XII were coupled in the presence of tetrabutylammonium fluoride (dried from THF) or tetrabutylammonium fluoride hydrate. In Examples 17, 19 and 21–24, Compound X was used in the form of its hydrochloride salt. The results are shown below in Table 2:

The following Examples 25–28 relate to the reaction of Compound X with Compound XII in the presence of fluoride and various organic bases.

EXAMPLES 25–28

Following the procedure of Example 8a, above, but with some reagent substitutions shown below, Compound X and Compound XII were coupled in the presence of fluoride ion and various organic bases. All reactions below were performed in N-methylpyrrolidinone solvent. The results are shown below in Table 3:

TABLE 2

| Example | F⁻ | F⁻:Compound X Ratio | Solvent | Base | Conditions | % Conversion (HPLC) |
|---|---|---|---|---|---|---|
| 16 | TBAF | 2:1 | NMP | lutidine (1 eq.) | 120° C./1 h | 68.8 |
| 17* | TBAF | 4:1 | NMP | lutidine (2 eq.) | 120° C./1 h | 69.6 |
| 18 | TBAF | 2:1 | NMP | lutidine (2 eq.) | 120° C./2 h | 90.1 |
| 19* | TBAF.XH₂O | 2:1 | NMP | lutidine (2 eq.) | 120° C./4 h | 55.7 |
| 20 | TBAF.XH₂O | 2:1 | NMP | lutidine (1 eq.) | 130° C./1.5 h | 83.1 |
| 21* | TBAF.XH₂O | 1:1 | NMP | lutidine (1 eq.) | 130° C./1 h | 56.0 |
| 22* | TBAF.XH₂O | 2:1 | ⁿBuOH | lutidine (2 eq.) | 122° C./6 h | 56.8 |
| 23* | CsF | 2:1 | NMP | lutidine (2 eq.) | 120° C./6 h | 4.7 |
| 24* | TBAF | 2:1 | NMP | lutidine (2 eq.) | 120° C./1 h | 76.3 |

*Compound X used as hydrochloride salt
TBAF = tetrabutylammonium fluoride (dried from THF solution)
TBAF.XH₂O = tetrabutylammonium fluoride hydrate
NMP = N-methylpyrrolidinone
ⁿBuOH = n-butanol As can be seen in Table 2, the rate of reaction between Compound X and Compound XII when the fluoride ion was tetrabutylammonium fluoride (dried from 1.0M THF) was slightly faster than that when the fluoride ion was tetrabutylammonium fluoride hydrate. In addition, that Compound X was used as its acid salt did not appear to significantly affect its rate of reaction.

TABLE 3

| Example | F⁻ | F⁻: Compound X Ratio | Solvent | Base | Conditions | % Conversion (HPLC) |
|---|---|---|---|---|---|---|
| 25 | TBAF | 2:1 | NMP | N-methyl-imidazole | 120° C./1 h | 27.9 |
| 26 | TBAF.XH$_2$O | 2:1 | NMP | lutidine (2 eq.) | 120° C./1 h | 52.8 |
| 27 | TBAF.XH$_2$O | 2:1 | NMP | Et$_3$N (2 eq.) | 120° C./1 h | 46.7 |
| 28 | TBAF.XH$_2$O | 2:1 | NMP | iPr$_2$Net (2 eq.) | 120° C./1 h | 53.0 |

TBAF = tetrabutylammonium fluoride (dried from THF solution)
THF = tetrahydrofuran
NMP = N-methylpyrrolidinone As shown in Table 3, the effectiveness of the various organic bases in relation to rate of reaction of Compound X with Compound XII is as follows: lutidine ~iPr$_2$NEt>Et$_3$N>N-methylimidazole. A similar reaction with collidine, not shown in Table 3, showed that collidine is about as effective as lutidine and iPr$_2$NEt.

The following Examples 29–37 relate to the reaction of Compound X with Compound XII in the presence of fluoride and various ethereal or alcoholic solvents.

EXAMPLES 29–37

Following the procedure of Example 8a, above, but with some reagent substitutions shown below, Compound X and Compound XII were coupled in the presence of fluoride ion and various ethereal or alcoholic solvents. The results are shown below in Table 4:

TABLE 4

| Example | F | F: Compound X Ratio | Solvent | Base | H$_2$O | Conditions | % Conversion (HPLC) |
|---|---|---|---|---|---|---|---|
| 29 | CsF | 1:1 | A | — | — | 120° C./18 h | 27.1 |
| 30 | KF | 1:1 | A | — | — | 120° C./18 h | 9.23 |
| 31 | CsF | 1:1 | B | — | — | 120° C./18 h | 71.5 |
| 32 | CsF | 1:1 | C | — | — | 120° C./18 h | 43.0 |
| 33 | CsF | 1:1 | D | — | — | 120° C./18 h | 37.7 |
| 34 | CsF | 1:1 | E | — | — | 120° C./18 h | 60.9 |
| 35 | CsF | 1:1 | F | — | — | 120° C./18 h | 37.2 |
| 36 | CsF | 1:1 | F | lutidine (1 eq.) | — | 120° C./24 h | 89.6 |
| 37(a) | CsF | 1:1 | C | lutidine (1 eq.) | — | 120° C./24 h | 89.0 |
| 37(b)* | KF | 0.3:1 | G | lutidine (1 eq.) | — | 124–27° C./6 h | 94.8 |
| 37(c)* | KF | 0.3:1 | G | lutidine (1 eq.) | — | 124–27° C./6 h | 95.2 |
| 37(d)* | KF | 0.3:1 | G | lutidine (1 eq.) | — | 124–27° C./6 h | 94.4 |
| 37(e)* | KF | 0.3:1 | G | lutidine (1 eq.) | 1% | 124–27° C./4.5 h | 94.7 |
| 37(f)* | KF | 0.3:1 | G | lutidine (1 eq.) | 1% | 124–27° C./4 h | 93.9 |
| 37(g)* | KF | 0.3:1 | G | lutidine (1 eq.) | 3% | 124–27° C./5 h | 93.7 |
| 37(h)* | KF | 0.3:1 | G | lutidine (1 eq.) | 5% | 124–27° C./5 h | 92.1 |

*Compound X used as hydrochloride salt
A = (CH$_3$OCH$_2$CH$_2$)$_2$O
B = (HOCH$_2$CH$_2$)$_2$O
C = CH$_3$OCH$_2$CH$_2$OCH$_2$CH$_2$OH
D = CH$_3$CH$_2$CH$_2$CH$_2$OCH$_2$CH$_2$OH
E = CH$_3$OCH$_2$CH$_2$OH
F = CH$_3$CH$_2$CH$_2$CH$_2$OH
G = CH$_3$OCH$_2$CH$_2$OCH$_3$ As shown in Table 4, significant amounts of the product of Compound X and Compound XII are obtained when the reaction is performed in the presence of fluoride ion and etheral or alcoholic solvent. It appears, however, that when CsF or KF is used as the fluoride source, the conversion percentages are not as high as those obtained when TBAF or TBAF.XH$_2$O is used, particularly in conjunction with non-ethereal solvents (Tables 1–3).

The following Examples 38–40 relate to the reaction of Compound X with Compound XII in the presence of KF/CaF$_2$ and various solvents.

EXAMPLES 38–40

Following the procedure of Example 8a, above, but with some reagent substitutions shown below, Compound X and Compound XII were coupled in the presence of KF/CaF$_2$ (Aldrich Chemical Co., Milwaukee, Wis.) and various solvents. The results are shown below in Table 5:

TABLE 5

| Example | F⁻ | F⁻: Compound X Ratio | Solvent | Base | Conditions | % Conversion (HPLC) |
|---------|-----|------|---------|------|------------|---------------------|
| 38* | KF/CaF$_2$ | 2:1 | ⁿBuOH | lutidine (2 eq.) | 122° C./4 h | 87.0 |
| 39* | KF/CaF$_2$ | 2:1 | NMP | lutidine (2 eq.) | 122° C./1 h | 24.0 |
| 40* | KF/CaF$_2$ | 0.5:1 | ⁿBuOH | lutidine (2 eq.) | 122° C./5 h | 77.7 |

*Compound X used as hydrochloride salt
ⁿBuOH = n-butanol
NMP = N-methylpyrrolidinone As shown in Table 5, significant amounts of the product of Compound X and Compound XII were obtained when the reaction is performed in the presence of KF/CaF$_2$ and ⁿBuOH or NMP. It appears, however, that when CsF or KF is used as the fluoride source, the conversion percentages are not as high as those obtained when TBAF or TBAF.XH$_2$O is used, particularly in conjunction with non-ethereal solvents (Tables 1–3).

The following Examples 41–43 relate to the synthesis of norastemizole via fluoride ion activation (Scheme 8), and intermediates useful therefor.

EXAMPLE 41

Compound XXII. In a 100 mL flask was placed 7 g (46 mmol) of 4-piperidone hydrate hydrochloride and 125 mL of methylene chloride. The resulting suspension was cooled to 0° C., whereupon 27 mL (4.1 eq., 188 mmol) of triethylamine were added. To the resulting mixture was added, dropwise, 16 mL (3.0 eq., 138 mmol) of trimethylacetyl chloride at 0° C. The resulting mixture was allowed to warm to 40° C. and stir overnight. The resulting mixture was diluted with tert-butyl methyl ether, and filtered. The filtrate was concentrated, and the resulting residue was dissolved in 250 mL of tert-butyl methyl ether. The tert-butyl methyl ether solution was washed with 1N HCl (100 mL), water (100 mL), 2N Na$_2$CO$_3$ (100 mL) and brine, and then dried (Na$_2$SO$_4$). The tert-butyl methyl ether was removed in vacuo to afford 12.5 g of an oil which contained a 1:1 mixture of trimethylacetic anhydride and N-trimethylacetyl-4-piperidone, as verified by $^1$H NMR. The oil was crystallized from hexane to afford 2.0 g of pure N-trimethylacetyl-4-piperidone. The mother liquor from the hexane crystallization was purified via silica gel chromatography to provide an additional 2.1 g of N-trimethylacetyl-4-piperidone: $^1$H NMR (300 MHz, CDCl$_3$) δ3.91 (dd, 4H, J=6.3, 6.3 Hz), 2.48 (dd, 4H, J=6.3, 6.3 Hz), 1.36 (s, 9H); $^{13}$C NMR (75 MHz, CDCl$_3$) δ206.95, 176.59, 44.13, 41.23, 38.77, 28.23.

3.0 g (16 mmol) of the N-trimethylacetyl-4-piperidone obtained according to the procedure above and 1.2 g (17 mmol) of hydroxylamine hydrochloride were placed into a 50 mL flask with 20 mL of ethanol. To the resulting mixture was added 1.9 g (18 mmol) of Na$_2$CO$_3$, and the resulting mixture was allowed to stir at room temperature overnight. The ethanol was removed in vacuo, and the resulting solid was triturated with ethyl acetate (2×50 mL). Combined ethyl acetate washings were washed with water (30 mL) and brine (30 mL), and dried (Na$_2$SO$_4$). The ethyl acetate solution was concentrated to yield 2.4 g (74%) of N-trimethylacetyl-4-hydroxyiminopiperidine as a white solid: $^1$H NMR (300 MHz, CDCl$_3$) δ3.75 (dd, 4H, J=12.3, 6.2 Hz), 2.68 (dd, 2H, J=6.2, 6.2 Hz), 2.39 (dd, 2H, J=6.2, 6.1 Hz), 1.36 (s, 9H); $^{13}$C NMR (75 MHz, CDCl$_3$) δ176.66, 156.34, 45.02, 43.51, 38.77, 31.13, 28.31, 24.93.

1.7 g (8.5 mmol) of the N-trimethylacetyl-4-hydroxyiminopiperidine obtained above was placed into a reaction vessel and to it was added 20 mL of ethanol containing 2 mL of CHCl$_3$. 200 mg of PtO$_2$ was added to the reaction vessel, and the reaction vessel was placed under 50 psi of H$_2$ and shaken at room temperature for 4 h. The resulting reaction mixture was filtered and the filtrate was concentrated to afford 1.5 g (80%) of the title compound, in the form of its hydrochloride salt, as a white solid. The solid was partitioned between 100 mL of methylene chloride and 10 mL of 2N NaOH. The methylene chloride layer was separated and concentrated in vacuo to afford 800 mg of Compound XXII as a clear oil: $^1$H NMR (300 MHz, CDCl$_3$) δ4.37 (d, 2H, J=13 Hz), 2.97 (m, 1H), 2.88 (dd, 2H, J=11.4, 11.4 Hz), 2.2 (s, 2H), 1.80 (d, 2H, J=12.8 Hz), 1.28 (s, 9H), 1.28 (m, 2H); $^{13}$C NMR (75 MHz, CDCl$_3$) δ175.18, 47.98, 43.13, 37.86, 35.01, 27.66.

EXAMPLE 42

To a 25 mL 3-neck flask equipped with a thermometer, reflux consenser and stir bar were added, under a nitrogen atmosphere, 885.6 mg (4.8 mmol) of Compound XXII, obtained according to the procedure of Example 41, and 0.93 mL (8.0 mmol) of lutidine. The mixture was heated to 120° C., whereupon a solution of 1.04 g (4 mmol., 1 eq.) of Compound X (Aldrich Chemical Co., Milwaukee, Wis.), 8 mmol of tetrabutylammonium fluoride (obtained from its 1.0M THF solution by distillation under vacuum with anhydrous toluene) and 4 mL of N-methylpyrrolidinone was added slowly over 2 h. The reaction mixture was allowed to stir at 120° C. for 1 h. High-performance liquid chromatography revealed >95% coversion to Compound XXIII. The reaction mixture was allowed to cool to ambient temperature, and slowly poured into a solution of 5% aqueous NaOH while stirring. The resulting suspension was allowed to stir at 0°–10° C. for 30 minutes, and the resulting solid product was collected by vacuum filtration, washed with water (3×5 mL), and air dried for 30 minutes under vacuum to afford crude Compound XXIII: $^1$H NMR (300 MHz, CDCl$_3$) δ7.52 (1H, d, J=7.8 Hz), 7.20–7.00 (7H, m, two groups), 5.13 (2H, s), 4.40 (1H, NH br. d), 4.32 (2H, pseudo d), 4.20 (1H, m), 3.00 (2H, pseudo t), 2.15 (2H, pseudo d), 1.30 (2H, m overlapped), 1.26 (9H, s); $^{13}$C NMR (75 MHz, CDCl$_3$) δ176.3, 164.2 and 161.0 ($^{13}$C-$^{19}$F coupling), 153.3, 142.4, 134.6, 131.4, 128.4, 121.7, 120.0, 116.6, 116.4, 116.1, 107.5, 50.5, 45.1, 44.2, 38.9, 33.1, 28.6. It is to be noted that under the same reaction conditions as above, but without the use of tetrabutylammonium fluoride, only 3.5% conversion (high-performance liquid chromatography) to Compound XXIII was achieved after 3 h at 120° C.

The Compound XXIII obtained above was placed in a 50 mL, 3-neck flask equipped with a thermometer, reflux condenser and stir bar. 5 mL of 48% hydrobromic acid was added, and the resulting mixture was heated to 110° C. and allowed to stir at that temperature for 2 h. After the reaction was complete (>98% conversion to norastemizole as shown by high-performance liquid chromatography), the reaction mixture was allowed to cool to room temperature, and 10 mL of toluene and 10 mL of water were added, with stirring. The resulting mixture was allowed to cool to 0°–5° C., and 50% aqueous NaOH was slowly added until the pH of the mixture was >11. The resulting slurry was allowed to stir at ambient temperature for 1 hour, and was then filtered under vacuum. The resulting wet cake was thoroughly washed with water (3×5 mL) and toluene (2×5 mL), and was air dried for 30 minutes. The resulting material was further dried at 25° C./5–10 mm Hg for 6–10 hours to afford 1.01 g of norastemizole in 77% overall yield from Compound X. The structure of norastemizole was confirmed by $^1$H NMR.

EXAMPLE 43

Norastemizole. To a 25 mL 3-neck flask equipped with a thermometer, ref lux consenser and stir bar were added, under a nitrogen atmosphere, 822 mg (4.8 mmol) of Compound XVI, obtained according to the procedure of Example 6, and 0.93 mL (8.0 mmol) of lutidine. The mixture was heated to 120° C., whereupon a solution of 1.04 g (4 mmol., 1 eq.) of Compound X (Aldrich Chemical Co., Milwaukee, Wis.), 8 mmol of tetrabutylammonium fluoride (obtained from its 1.0M THF solution by distillation under vacuum with anhydrous toluene) and 4 mL of N-methylpyrrolidinone was added slowly over 2 h. The reaction mixture was allowed to stir at 120° C. for 2 h. High-performance liquid chromatography revealed >95% coversion to Compound XVIII. The reaction mixture was allowed to cool to ambient temperature, and slowly poured into a solution of 5% aqueous NaOH while stirring. The resulting suspension was allowed to stir at 0°–10° C. for 30 minutes, and the resulting solid product was collected by vacuum filtration, washed with water (3×5 mL), and air dried for 30 minutes under vacuum to afford a crude mixture of Compound XVIII and 6% (HPLC) of migration product Compound XIX. NMR data for Compound XVIII: $^1$H NMR (300 MHz, DMSO-d$_6$) δ7.30–7.02 (6H, m two groups), 6.95 (1H, pseudo t, J=7.8, 2.3 Hz), 6.85 (1H, pseudo t, J=7.8, 2.3 Hz), 5.35 (2H, s), 4.33 (1H, pseudo d), 4.02 (1H, m), 3.83 (1H, pseudo d), 3.17 (1H, pseudo t), 2.75 (1H, pseudo t), 2.02 (3H, s), 2.0 (2H, m overlapped), 1.45 (2H, m); $^{13}$C NMR (75 MHz, DMSO-d$_6$) δ168.0, 163.0 and 159.7 ($^{13}$C-$^{19}$F coupling), 153.9, 142.8, 134.3, 133.5, 129.1, 129.0, 128.2, 120.5, 118.4, 115.5, 115.2, 107.9, 44.8, 43.7, 32.3, 31.5, 21.4. It is to be noted that under the same reaction conditions as above, but without the use of tetrabutylammonium fluoride, only 4.9% conversion (high-performance liquid chromatography) to Compound XVIII was achieved after 3 h at 120° C. In addition, without the use of tetrabutylammonium fluoride, the ratio of Compound XVIII:Compound XIX was 4:1.

The mixture of Compound XVIII obtained above was placed in a 50 mL, 3-neck flask equipped with a thermometer, reflux condenser and stir bar. 5 mL of 6N hydrochloric were added, and the resulting mixture was heated to 110° C. and allowed to stir at that temperature for 5 h. After the reaction was complete (>98% conversion to norastemizole as shown by high-performance liquid chromatography), the reaction mixture was allowed to cool to room temperature, and 10 mL of toluene and 10 mL of water were added, with stirring. The resulting mixture was allowed to cool to 0°–5° C., and 50% aqueous NaOH was slowly added until the pH of the mixture was >11. The resulting slurry was allowed to stir at ambient temperature for 1 hour, and was then filtered under vacuum. The resulting wet cake was thoroughly washed with water (3×5 mL) and toluene (2×5 mL), and was air dried for 30 minutes. The resulting material was further dried at 25° C./5–10 mm Hg for 10 hours to afford 925 mg of norastemizole (71% overall yield from Compound X), which contained 5.6% of iso-norastemizole.

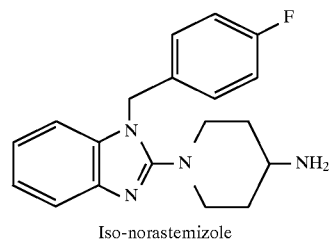

Iso-norastemizole

The structure of norastemizole was confirmed by $^1$H and $^{13}$C NMR. NMR data for iso-norastemizole: $^1$H NMR (300 MHz, CDCl$_3$) δ7.61 (1H, d, J=7.8 Hz), 7.43–7.29 (5H, m), 7.25 (2H, m), 5.47 (2H, s), 3.90 (2H, pseudo d), 3.55 (2H, NH$_2$ br. s), 3.35 (2H, pseudo t), 2.08 (2H, pseudo d), 1.80 (2H, pseudo t); $^{13}$C NMR (75 MHz, CDCl$_3$) δ163.3 and 160.1 ($^{13}$C-$^{19}$F coupling), 151.9, 131.9, 130.9, 129.6, 128.8, 128.7, 124.5, 123.9, 116.0, 115.7, 112.5., 111.6, 48.2, 47.8, 46.4, 28.9.

The following Examples 44–54 relate to the synthesis of norastemizole via sulfonyl group and fluoride ion activation (Scheme 9), and intermediates useful therefor.

EXAMPLE 44

Compound XXV. To a 250 mL, 3-neck flask equipped with a thermometer and stirring bar were added 15.2 g (100 mmol) of 2-chlorobenzimidazole (Compound XXIV), 50 mL of dimethylformamide and 16 g (150 mmol) of sodium carbonate, under a blanket of nitrogen. To the resulting mixture was added 21 g (110 mmol) of p-toluenesulfonyl chloride, with stirring. The resulting slurry was allowed to stir at room temperature for 2 h. The course of the reaction was monitored using high performance liquid chromatography. The reaction mixture was slowly poured, with vigorous stirring, into an Erlenmeyer flask containing 500 mL of water. The resulting slurry was cooled to 0°–5° C. and was allowed to stir at that temperature for 2 h. The resulting crystalline solid was collected by vacuum filtration, washed with water (4×50 mL) and air dried for 30 minutes. The resulting wet solid was dried at 40°–50° C./5–10 mm Hg for 14 h to provide 29.7 g (97%) of Compound XXV as an off-white solid: $^1$H NMR (300 MHz, CDCl$_3$) δ8.13 (1H, d, J=8.1 Hz), 7.92 (2H, m), 7.65 (1H, d, J=8.0 Hz), 7.42–7.13 (4H, m), 2.39 (3H, s); $^{13}$C NMR (75 MHz, CDCl$_3$) δ146.78, 140.94, 138.4, 134.6, 133.8, 130.4, 127.6, 125.7, 125.3, 119.9, 113.9, 21.8.

EXAMPLE 45

2-Chloro-1-N-methylsulfonylbenzimidazole. 2-Chloro-1-N-methylsulfonylbenzimidazole was prepared according to the method of Example 44, above, except that methylsulfonyl chloride was used in place of p-toluensulfonyl chloride: $^1$H NMR (300 MHz, CDCl$_3$) δ7.90 (1H, m), 7.68 (1H, m), 7.39 (2H, m), 3.42 (3H, s); $^{13}$C NMR (75 MHz, CDCl$_3$) δ140.8, 137.9, 133.7, 125.9, 125.4, 120.1, 113.7, 42.8.

EXAMPLE 46

2-Chloro-1-N-tert-butoxycarbonylbenzimidazole. 2-Chloro-1-N-tert-butoxycarbonylbenzimidazole was prepared according to the method of Example 44, above, except that di-tert-butyl dicarbonate (Aldrich Chemical Co., Milwaukee, Wis.) was used in place of p-toluensulfonyl chloride: $^1$H NMR (300 MHz, CDCl$_3$) δ7.93 (1H, m), 7.67 (1H, m), 7.40 (2H, m), 1.73 (9H, s); $^{13}$C NMR (75 MHz, CDCl$_3$) δ147.5, 141.5, 139.8, 133.7, 125.2, 124.8, 119.6, 114.9, 86.8, 28.1.

EXAMPLE 47

2-Chloro-1-N-p-methoxybenzenesulfonylbenzimidazole. 2-Chloro-1-N-p-methoxybenzenesulfonylbenzimidazole was prepared according to the method of Example 44, above, except that p-methoxybenzenesulfonyl chloride was used in place of p-toluensulfonyl chloride: $^1$H NMR (300 MHz, CDCl$_3$) δ8.14 (1H, d, J=8.7 Hz), 7.98 (2H, 2×d overlapped, J=8.7 Hz), 7.66 (1H, d, J=8.7 Hz), 7.40 (2H, m), 6.99 (2H, 2×d overlapped, J=8.7 Hz), 3.87 (3H, s); $^{13}$C NMR (75 MHz, CDCl$_3$) δ141.0, 138.5, 133.9, 130.1, 128.9, 125.7, 125.2, 119.9, 115.0, 114.0, 56.0.

EXAMPLE 48

2-Chloro-1-N-o-nitrobenzenesulfonylbenzimidazole. 2-Chloro-1-N-o-nitrobenzenesulfonylbenzimidazole was prepared according to the method of Example 44, above, except that o-nitrobenzenesulfonyl chloride was used in place of p-toluensulfonyl chloride: $^1$H NMR (300 MHz, CDCl$_3$) δ8.34 (1H, d, J=6.9 Hz), 7.99 (1H, d, J=6.9 Hz), 7.90 (3H, m), 7.78 (1H, m), 7.46 (2H, m); $^{13}$C NMR (75 MHz, CDCl$_3$) δ148.1, 140.4, 137.2, 136.5, 134.7, 132.8, 131.2, 126.1, 125.8, 125.6, 123.5, 120.1, 114.8.

EXAMPLE 49

Compound XXVI. To a 25 mL 3-neck flask equipped with a thermometer, reflux consenser and stir bar are added, under a nitrogen atmosphere, 822 mg (4.8 mmol) of Compound XII (Lancaster Synthesis, Inc., Windham, N.H.), and 0.93 mL of lutidine. The mixture is heated to 120° C., whereupon a solution of 4 mmol. (1 eq.) of Compound XXV, obtained according to the procedure of Example 44, 8 mmol of tetrabutylammonium fluoride (obtained from its 1.0M THF solution by distillation under vacuum with anhydrous toluene) and 4 mL of N-methylpyrrolidinone are added slowly over 2 h. The reaction mixture is allowed to stir at 120° C. for 1 h. The reaction mixture is allowed to cool to ambient temperature, and is slowly poured into a solution of 5% aqueous NaOH while stirring. The resulting suspension is allowed to stir at 0°–10° C. for 30 minutes, and the resulting solid product is collected by vacuum filtration, washed with water (3×5 mL), and air dried for 30 minutes under vacuum to afford Compound XXVI.

EXAMPLE 50

Compound XXVII: Method A. To a 25 mL, 3-neck flask equipped with a thermometer and stirring bar were added 45 mg (0.1 mmol) of Compound XXVI, obtained by the procedure of Example 49, above, 0.5 mL of dimethylformamide, 18.4 mg (0.2 mmol) of HSCH$_2$COOH and 20 mg of LiOH, under a blanket of N$_2$. The resulting mixture was allowed to stir at 50°–60° C. for 5–10 minutes. The reaction mixture was allowed to cool to 22° C., whereupon 10 mL of 10% aqueous Na$_2$CO$_3$ was added. The resulting mixture was allowed to stir at 0°–50° C. for 3 h. The resulting solid was collected by vacuum filtration, washed with heptane (2×5 mL) and dried at 40°–5° C. (5–10 mm/Hg) for 12 h to afford 28 mg (97.5%) Compound XXVII: $^1$H NMR (300 MHz, DMSO-d$_6$) δ10.60 (1H, br. s), 7.16 (2H, m), 6.88 (2H, m), 6.61 (1H, d, J=7.1 Hz), 4.07 (2H, q, J=7.0 Hz), 4.00 (2H, pseudo d), 3.82 (1H, m), 2.96 (2H, m), 1.96 (2H, pseudo d), 1.42 (2H, pseudo d), 1.12 (3H, t, J=7.0 Hz); $^{13}$C NMR (75 MHz, DMSO-d$_6$) δ154.6, 122.3, 119.1, 114.3, 114.0, 60.7, 49.1, 42.5, 31.8, 14.6.

EXAMPLE 51

Compound XXVII: Method B. To a 50 mL 3-neck flask equipped with a thermometer, reflux consenser and stir bar were added, under a nitrogen atmosphere, 3.04 g (20 mmol, 1 eq.) of Compound XXIV, 5.1 g (30 mmol) of Compound XII and 10 mL of ethylene glycol. The reaction mixture was allowed to stir at 115°–120° C. for 24 h, at which point high-performance liquid chromatography indicated that the reaction was complete. The reaction mixture was allowed to cool to ambient temperature, and poured into a mixture of 20 mL of toluene and 50 mL of water with vigorous stirring. The resulting mixture was allowed to sit for 30 minutes. The resulting solid was collected by vacuum filtration, washed with water (2×10 mL) and toluene (2×10 mL) and dried at 50°–60° C. (5–10 mm/Hg) for 12 h to afford 4.8 g (84%) of Compound XXVII as a pale yellow powder. $^1$H and $^{13}$C data were consistent with $^1$H and $^{13}$C data obtained from Compound XXVII obtained from Example 50, above.

EXAMPLE 52

Compound XIVa (free base): Method A. To a 25 mL 3-neck flask equipped with a thermometer and stir bar were added, under a nitrogen atmosphere, 1.0 g (3.5 mmol) of Compound XXVII obtained by the procedure of Example 51 above, 392 mg (7 mmol) of KOH powder and 5 mL of dimethylformamide. 0.48 mL (3.85 mmol) of 4-fluorobenzyl bromide was then added, and the reaction mixture was allowed to stir at 50° C. for 30 minutes. After cooling to room temperature, the reaction mixture was poured into 30 mL of a 10% aqueous Na$_2$CO$_3$ solution, and was allowed to stir at ambient temperature for 30 minutes. The resulting solid was collected by vacuum filtration, washed with water (2×10 mL) and heptane (2×10 mL) and dried at 50°–60° C. (5–10 mm/Hg) for 14 h to afford 1.31 g (96%) of Compound XIVa (free base) as an off-white powder. $^1$H and $^{13}$C data were consistent with $^1$H and $^{13}$C data obtained from Compound XIVa (free base) obtained from Example 8a, above.

EXAMPLE 53

Compound XIVa (free base): Method B. To a 500 mL, 3-neck flask equipped with a thermometer, reflux condenser and stirring bar were added 23.8 g (80 mmol, 1.0 eq.) of Compound X (hydrochloride salt), 1.39 g (24.0 mmol) of KF, 1.6 g (4.0 mmol) of trioctylmethylammonium chloride and 32 mL of CH$_3$OCH$_2$CH$_2$OCH$_2$CH$_2$OH, under an atmosphere of N$_2$. To the resulting mixture was added 11.2 mL (96 mmol) of lutidine over 3 minutes with stirring, whereupon the temperature of the reaction mixture rose to 45° C.

The resulting mixture was allowed to stir at 30°–40° C. for 10–15 minutes. To the resulting mixture was added 16.4 g (96 mmol) of Compound XII over 2–3 minutes. The resulting mixture was heated to 122°–125° C. over 20–30 minutes, and was allowed to stir at that temperature for 7 h. HPLC revealed >98% conversion to Compound XIVa (free base). The reaction mixture was allowed to cool to 50°–60° C., and was diluted with 80 mL of toluene and 200 g of a 4% aqueous NaOH solution. The resulting mixture was allowed to stir at 30°–40° C. for 10–15 minutes (Vmax=370 mL). The mixture was allowed to cool to 0°–5° C., and was allowed to stir at that temperature for 2–3 hours. The resulting solid was collected by vacuum filtration, washed with water (3×20 mL) and air dried for 20 minutes to afford 27.5 g (85%) of Compound XIVa (free base) having $^1$H and $^{13}$C NMR data consistent with that of Compound XIVa (free base) obtained from the procedure of Example 8a, above.

EXAMPLE 54

Norastemizole. Compound XIVa (free base), obtained according to the procedure of Example 52 above, was hydrolyzed according to the procedure of Example 8a, except that concentrated NaOH in ethanol was used at 78°–82° C. for 14–24 h, to afford norastemizole.

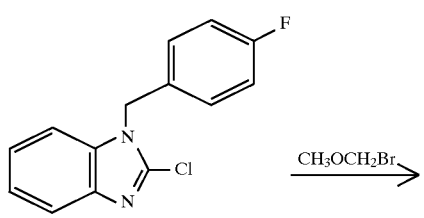

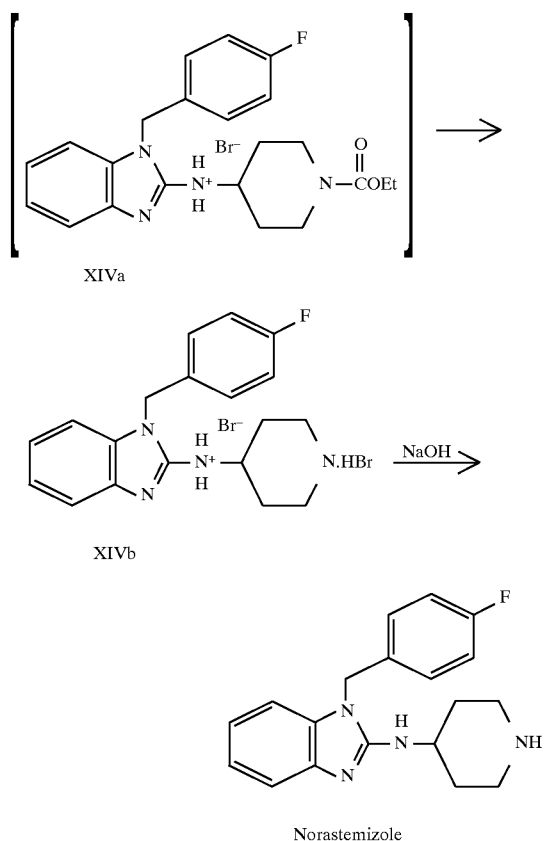

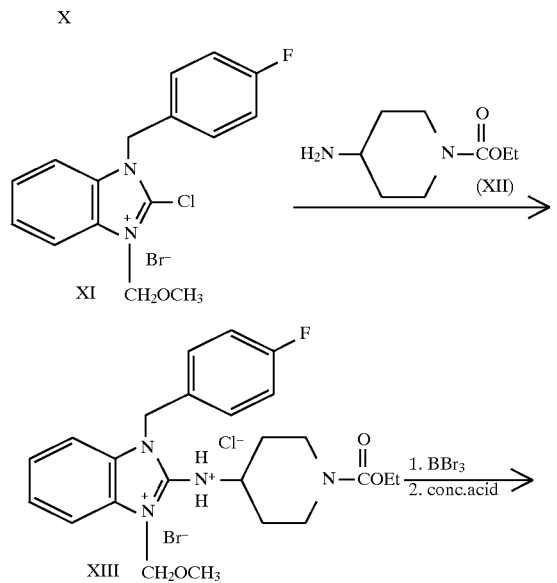

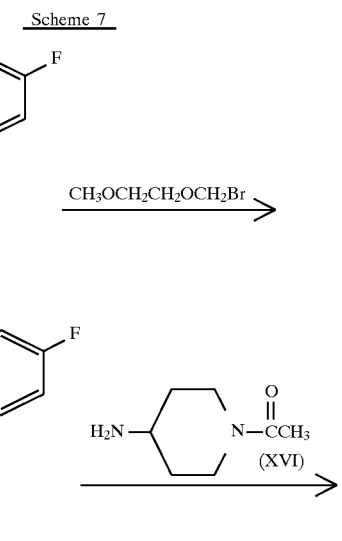

-continued
Scheme 7
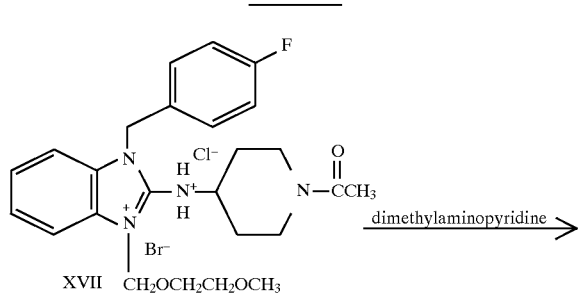
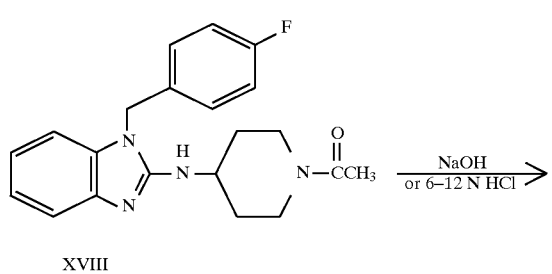
Norastemizole
Scheme 8
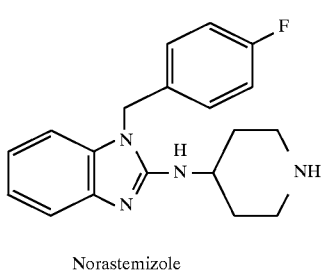
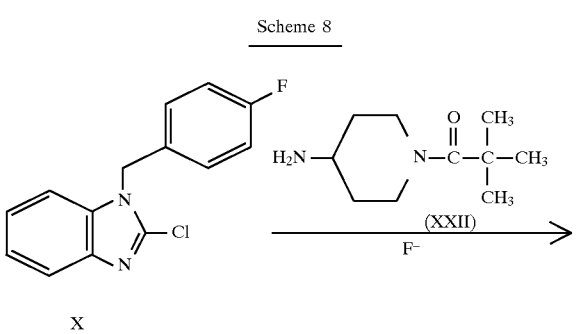
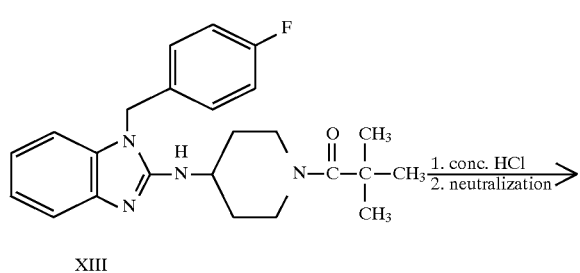
XIII
-continued
Scheme 8
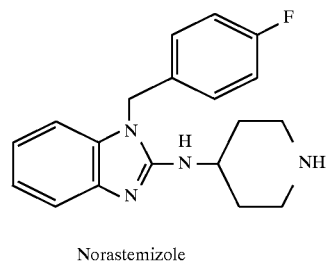
Norastemizole
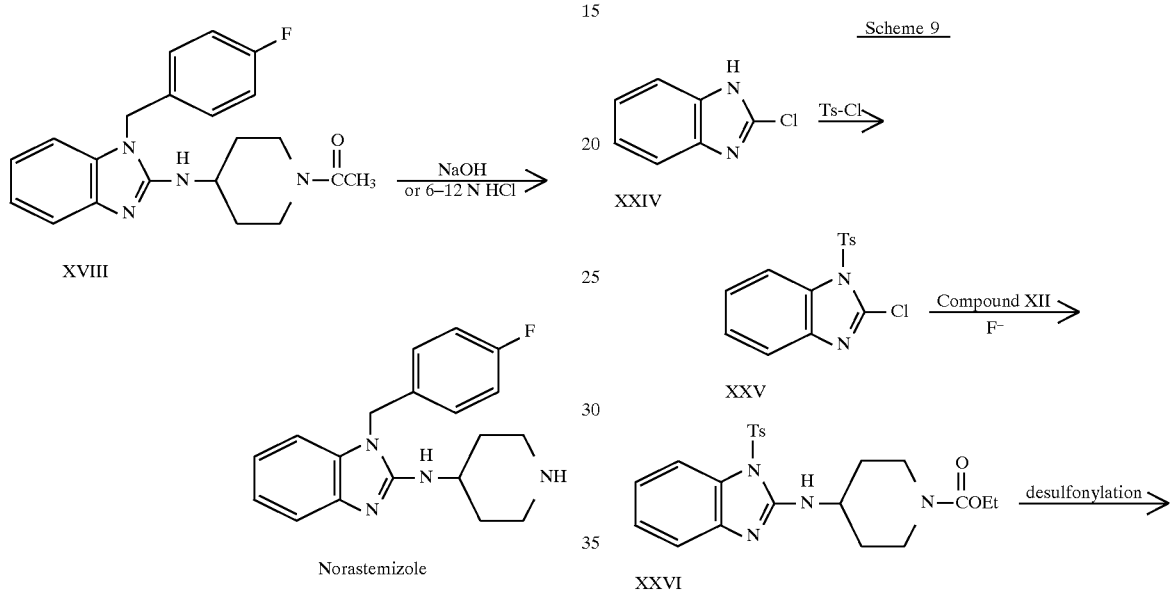
Scheme 9
XIVa (free base)
Norastemizole The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A method for synthesizing a 2-substituted imidazole, comprising:
    (a) reacting an imidazole having a leaving group in the 2-position thereof with an alkylating agent to afford a 3-N-alkylated imidazolium salt having an alkyl group in the 3-N-position and a leaving group in the 2-position thereof;
    (b) reacting the 3-N-alkylated imidazolium salt with a nucleophile to afford a 2-substituted 3-N-alkylated imidazolium salt, wherein the nucleophile (1) displaces said leaving group from the 2-position of the 2-substituted 3-N-alkylated imidazolium salt and (2) forms a bond with the 2-carbon atom thereof; and
    (c) reacting the 2-substituted 3-N-alkylated imidazolium salt with a hydrolytic or nucleophilic agent that removes the alkyl group from the 3-position of the 2-substituted 3-N-alkylated imidazolium salt to afford the 2-substituted imidazole.

2. The method according to claim 1, wherein the imidazole having a leaving group in the 2-position is of the formula I

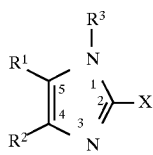

wherein:
    $R^1$, $R^2$ and $R^3$ are independently hydrogen, $C_1$–$C_2$ branched or straight chain alkyl, $C_3$–$C_8$ cycloalkyl, phenyl, naphthyl and benzyl, said $C_1$–$C_{12}$ branched or straight chain alkyl, $C_3$–$C_8$ cycloalkyl, phenyl, naphthyl and benzyl groups being optionally substituted with one or more halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), carboxyl, phenyl, —C(O)O—$C_1$–$C_6$ alkyl or —C(O)$C_1$–$C_6$ alkyl groups, except that $R^3$ is not —C(O)$C_1$–$C_6$ alkyl; or
    either $R^1$ and $R^2$, or $R^1$ and $R^3$, is joined to form a $C_3$–$C_8$ saturated or unsaturated cycloalkyl group, aromatic group, or heteroaromatic group, said $C_3$–$C_8$ saturated or unsaturated cycloalkyl group, aromatic group, or heteroaromatic group being unsubstituted or substituted with one or more members of the group consisting of halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), —S(O)$_2$($C_1$–$C_6$ alkyl), carboxyl, phenyl and —C(O)O—$C_1$–$C_6$ alkyl; or
    $R^1$ and $R^2$ are independently —NHC(O) ($C_1$–$C_6$ alkyl), —N($C_1$–$C_6$ alkyl)C(O) ($C_1$–$C_6$ alkyl), —C(O)NH ($C_1$–$C_6$ alkyl) or —C(O)N ($C_1$–$C_6$ alkyl) ($C_1$–$C_6$ alkyl); and
    X is selected from the group consisting of fluoro, chloro, bromo, iodo, —OSO$_2$CH$_3$, —OSO$_2$CF$_3$, —OSO$_2$C$_6$H$_4$-p-CH$_3$, —OSO$_2$C$_6$H$_4$-p-Br, —OC(O) ($C_1$–$C_6$ alkyl), —N$^+$($C_1$–$C_6$ alkyl) ($C_1$–$C_6$ alkyl) ($C_1$–$C_6$ alkyl) and —S$^+$($C_1$–$C_6$ alkyl) ($C_1$–$C_6$ alkyl).

3. The method according to claim 2, wherein the $C_3$–$C_8$ saturated or unsaturated cycloalkyl group, is selected from the group consisting of a substituted or unsubstituted cyclopropane, cyclobutane, cyclobutene, methylcyclobutane, cyclopentane, cyclopentene, cyclohexane, cyclohexene, methylcyclohexane and dimethylcyclohexane.

4. The method according to claim 2, wherein the aromatic group is selected from the group consisting of a substituted or unsubstituted benzene group, toluene group, and xylene group.

5. The method according to claim 2, wherein the heteroaromatic group is selected from the group consisting of thienyl, furyl, 2H-pyrrolyl, imidazolyl, pyrazolyl, pyridyl, pyrazinyl, pyrimidinyl and pyridazinyl.

6. The method according to claim 1, wherein the alkylating agent is a compound of the formula $R^4Y$;
    wherein $R^4$— is $R^5OCH_2$—, $R^5OCH_2CH_2OCH_2$—, $R^5SCH_2$—, $(R^5)_3SiCH_2CH_2OCH_2$—, $HOCH_2CH_2$—, $R^5OC(O)$—, $R^5OC(S)$—, $(R^5)(R^5)NC(O)$—, $(R^5)(R^5)(R^5)Si$—, $(R^5)(R^5)(R^5)Sn$—, $(R^5)(R^5)S(O)_2CH_2$—, $(R^5)(R^5)S(O)_2CH(R^5)$— and $(R^5)(R^5)S(O)_2C(R^5)(R^5)$—;
    —Y is fluoro, chloro, bromo, iodo, —OSO$_2$CH$_3$, —OSO$_2$CF$_3$, —OSO$_2$C$_6$H$_4$-p-CH$_3$, —OSO$_2$C$_6$H$_4$-p-Br, —CN, —O($C_1$–$C_6$ alkyl) and —OC(O) ($C_1$–$C_6$ alkyl); and
    each $R^5$ is independently $C_1$–$C_6$ straight or branched chain alkyl, $C_3$–$C_6$ cycloalkyl, ($C_1$–$C_6$ straight or branched chain alkyl)$_3$Si($C_1$–$C_6$ straight or branched chain alkyl), ($C_3$–$C_6$ cycloalkyl)$_3$Si($C_1$–$C_6$ straight or branched chain alkyl), $C_1$–$C_6$ straight or branched chain alkyl-C(O)— or, when $R^5$ is bonded to a nitrogen atom, $C_1$–$C_6$ straight or branched chain alkyl-OC(O)—.

7. The method according to claim 6, wherein the leaving group in the 2-position of the 3-N-alkylated imidazolium salt is the same as —Y.

8. The method according to claim 1, wherein the nucleophile is NH$_3$, NH$_2$($C_1$–$C_6$ alkyl), NH$_2$($C_3$–$C_8$ cycloalkyl), NH$_2$(phenyl), NH$_2$(Het), NH($C_1$–$C_6$ alkyl) ($C_1$–$C_6$ alkyl), NH(phenyl) ($C_1$–$C_6$ alkyl), NH(Het) ($C_1$–$C_6$ alkyl), NH(phenyl) (phenyl), NH(phenyl) (Het), NH(Het) (Het), NH$_2$NH$_2$, MN$_3$, HO($C_1$–$C_6$ alkyl), HO($C_1$–$C_6$ alkenyl), HO ($C_1$–$C_6$ alkynyl), HO($C_3$–$C_8$ cycloalkyl), HO($C_3$–$C_8$ cycloalkenyl), HS($C_1$–$C_6$ alkyl), HS($C_1$–$C_6$ alkenyl), HS($C_1$–$C_6$ alkynyl), HS($C_3$–$C_8$ cycloalkyl), HS($C_3$–$C_8$ cycloalkenyl), HO-phenyl, HO-naphthyl, MSi($C_1$–$C_6$ alkyl) ($C_1$–$C_6$ alkyl) ($C_1$–$C_6$ alkyl), ($C_1$–$C_6$ alkyl)Mg (halogen), ($C_1$–$C_6$ alkenyl)Mg (halogen), ($C_1$–$C_6$ alkyl)Li, ($C_1$–$C_6$ alkenyl)Li, ($C_1$–$C_6$ alkyl)$_2$Zn, ($C_1$–$C_6$ alkenyl)$_2$Zn, ($C_1$–$C_6$ alkyl)CeCl$_2$, MZn($C_1$–$C_6$ alkyl) ($C_1$–$C_6$ alkyl) ($C_1$–$C_6$ alkyl), Br$^-$, I$^-$, F$^-$, MP($C_1$–$C_6$ alkyl)$_2$, HP($C_1$–$C_6$ alkyl)$_2$, H$_2$N($C_1$–$C_6$ alkyl), H$_2$N($C_1$–$C_6$ alkenyl) and H$_2$N($C_1$–$C_6$ alkynyl),
    wherein M is Na$^+$ Li$^+$, K$^+$ $^+$Mg(halogen), $^+$Mn(halogen), $^+$Zn(halogen), $^+$Sn(halogen),
    each Het is independently 2-pyrrolyl, 3-pyrrolyl, 2-imidazolyl, 4-imidazolyl, 5-imidazolyl, 3-pyrazolyl, 4-pyrazolyl, 5-pyrazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 3-isoxazolyl, 4-isoxazolyl, 5-isoxazolyl, 3-isothiazolyl, 4-isothiazolyl, 5-isothiazolyl, 2-imidazolidinyl, 4-imidazolidinyl, 3-pyrazolidinyl, 4-pyrazolidinyl, 2-piperidinyl, 3-piperidinyl, 4-piperidinyl, 2-piperazinyl, 3-piperazinyl, 4-piperazinyl, 2-morpholinyl or 3-morpholinyl, and the nucleophile being unsubstituted or substituted, at either a carbon atom or a heteroatom, with one or more halogen, hydroxyl, sulfhydryl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), carboxyl, phenyl, $C_1$–$C_6$ alkoxylcarbonyl and ($C_1$–$C_6$ alkyl)-CO groups.

9. The method according to claim 1, wherein the step of reacting the 2-substituted 3-N-alkylated imidazolium salt with the hydrolytic or nucleophilic agent comprises:

(i) reacting the 2-substituted 3-N-alkylated imidazolium salt with a boron trihalide to afford a dealkylation product; and (ii) reacting the dealkylation product with a mineral acid to afford the 2-substituted imidazole.

10. The method according to claim 9, wherein the 2-substituted imidazole is in the form of its 3-imidazolium acid salt.

11. The method according to claim 1, wherein the nucleophile has more than one nucleophilic group, and one of the nucleophilic groups of the nucleophile is protected with a protecting group.

12. The method according to claim 11, wherein the protecting group is acid-labile, and is removed in the step of reacting the 2-substituted 3-N-alkylated imidazolium salt with the hydrolytic or nucleophilic agent.

13. The method according to claim 11, wherein the protecting group is base-labile, and is not removed in the step of reacting the 2-substituted 3-N-alkylated imidazolium salt with the hydrolytic or nucleophilic.

14. The method according to claim 13, further comprising reacting the 2-substituted imidazole with base at pH of about 9 to about 14 to remove the protecting group from one of the nucleophilic groups of the nucleophile.

15. A method for synthesizing norastemizole, comprising:

(a) reacting a 1-(4-fluorophenylmethyl)-1H-benzimidazole having a leaving group in the 2-position with an alkylating agent to afford a 3-N-alkylated 1-(4-fluorophenylmethyl)-1H-benzimidazolium salt having a leaving group in the 2-position thereof;

(b) reacting the 3-N-alkylated 1-(4-fluorophenylmethyl)-1H-benzimidazolium salt with a 4-aminopiperidine having a protecting group on the 1-nitrogen atom thereof to afford a 2-(4-amino-1-N-protected piperidinyl)-substituted 3-N-alkylated 1-(4-fluorophenylmethyl)-1H-benzimidazolium salt, wherein the 4-aminopiperidine (1) displaces said leaving group from the 2-position of the 3-N-alkylated 1-(4-fluorophenylmethyl)-1H-benzimidazolium salt and (2) forms a bond with the 2-carbon atom thereof; and (c) reacting the 2-(4-amino-1-N-protected piperidinyl)-substituted 3-N-alkylated 1-(4-fluorophenylmethyl)-1H-benzimidazolium salt with a hydrolytic or nucleophilic agent that removes the alkyl group from the 3-position of the 2-(4-amino-1-N-protected piperidinyl)-substituted 3-N-alkylated 1-(4-fluorophenylmethyl)-1H-benzimidazolium salt to afford norastemizole.

16. The method according to claim 15, wherein the leaving group is fluoro, chloro, bromo, iodo, —$OSO_2CH_3$, —$OSO_2CF_3$, —$OSO_2C_6H_4$-p-$CH_3$, —$OSO_2C_6H_4$-p-Br, —OC(O) ($C_1$–$C_6$ alkyl), —$N^+$($C_1$–$C_6$ alkyl) ($C_1$–$C_6$ alkyl) ($C_1$–$C_6$ alkyl) or —$S^+$($C_1$–$C_6$ alkyl) ($C_1$–$C_6$ alkyl).

17. The method according to claim 15, wherein the alkylating agent is a compound of the formula $R^4Y$;

wherein $R^4$— is $R^5OCH_2$—, $R^5OCH_2CH_2OCH_2$—, $R^5SCH_2$—, $(R^5)_3SiCH_2CH_2OCH_2$—, $HOCH_2CH_2$—, $R^5OC(O)$—, $R^5OC(S)$—, $(R^5)(R^5)NC(O)$—, $(R^5)(R^5)(R^5)Si$—, $(R^5)(R^5)(R^5)Sn$—, $(R^5)(R^5)S(O)_2CH_2$—, $(R^5)(R^5)S(O)_2CH(R^5)$— and $(R^5)(R^5)S(O)_2C(R^5)(R^5)$—;

—Y is fluoro, chloro, bromo, iodo, —$OSO_2CH_3$, —$OSO_2CF_3$, —$OSO_2C_6H_4$-p-$CH_3$, —$OSO_2C_6H_4$-p-Br, —CN, —O($C_1$–$C_6$ alkyl) and —OC(O) ($C_1$–$C_6$ alkyl); and each $R^5$ is independently $C_1$–$C_6$ straight or branched chain alkyl, $C_3$–$C_6$ cycloalkyl, ($C_1$–$C_6$ straight or branched chain alkyl)$_3$Si($C_1$–$C_6$ straight or branched chain alkyl), ($C_3$–$C_6$ cycloalkyl)$_3$Si($C_1$–$C_6$ straight or branched chain alkyl), $C_1$–$C_6$ straight or branched chain alkyl-C(O)— or, when $R^5$ is bonded to a nitrogen atom, $C_1$–$C_6$ straight or branched chain alkyl-OC(O)—.

18. The method according to claim 17, wherein the leaving group in the 2-position of the 3-N-alkylated 1-(4-fluorophenylmethyl)-1H-benzimidazolium salt is the same as —Y.

19. The method according to claim 15, wherein the protecting group is a sulfonyl group, an acid labile alkyl group, an acyl or alkoxycarbonyl group.

20. The method according to claim 19, wherein the alkoxycarbonyl group is an ethoxycarbonyl group, and the acyl group is an acetyl or a trimethylacetyl group.

21. The method according to claim 15, wherein the step of reacting the 2-(4-amino-1-N-protected piperidinyl)-substituted 3-N-alkylated 1-(4-fluorophenylmethyl)-1H-benzimidazolium salt with the hydrolytic or nucleophilic agent comprises:

(i) reacting the 2-(4-amino-1-N-protected piperidinyl)-substituted 3-N-alkylated 1-(4-fluorophenylmethyl)-1H-benzimidazolium salt with a boron trihalide to afford a dealkylation product; and (ii) reacting the dealkylation product with a mineral acid to afford norastemizole.

22. The method according to claim 21, wherein norastemizole is in the form of its acid salt.

23. The method according to claim 15, wherein the protecting group is acid-labile, and is removed in the step of reacting the 2-(4-amino-1-N-protected piperidinyl)-substituted 3-N-alkylated 1-(4-fluorophenylmethyl)-1H-benzimidazolium salt with the hydrolytic or nucleophilic agent.

24. A method for synthesizing norastemizole, comprising:

(a) reacting a 1-(4-fluorophenylmethyl)-1H-benzimidazole having a leaving group in the 2-position with an alkylating agent to afford a 3-N-alkylated 1-(4-fluorophenylmethyl)-1H-benzimidazolium salt having a leaving group in the 2-position thereof;

(b) reacting the 3-N-alkylated 1-(4-fluorophenylmethyl)-1H-benzimidazolium salt with a 4-aminopiperidine having a protecting group on the 1-nitrogen atom thereof to afford a 2-(4-amino-1-N-protected piperidinyl)-substituted 3-N-alkylated 1-(4-fluorophenylmethyl)-1H-benzimidazolium salt, wherein the 4-aminopiperidine (1) displaces said leaving group from the 2-position of the 3-N-alkylated 1-(4-fluorophenylmethyl)-1H-benzimidazolium salt and (2) forms a bond with the 2-carbon atom thereof;

(c) reacting the 2-(4-amino-1-N-protected piperidinyl)-substituted 3-N-alkylated 1-(4-fluorophenylmethyl)-1H-benzimidazolium salt with a hydrolytic or nucleophilic agent that removes the alkyl group from the 3-position of the 2-(4-amino-1-N-protected piperidinyl)-substituted 3-N-alkylated 1-(4-fluorophenylmethyl)-1H-benzimidazolium salt to afford protected norastemizole; and (d) hydrolyzing the protected norastemizole to afford norastemizole.

25. The method according to claim 24, wherein the leaving group is fluoro, chloro, bromo, iodo, —$OSO_2CH_3$, —$OSO_2CF_3$, —$OSO_2C_6H_4$-p-$CH_3$, —$OSO_2C_6H_4$-p-Br, —OC(O) ($C_1$–$C_6$ alkyl), —$N^+$($C_1$–$C_6$ alkyl) ($C_1$–$C_6$ alkyl) ($C_1$–$C_6$ alkyl) or —$S^+$($C_1$–$C_6$ alkyl) ($C_1$–$C_6$ alkyl).

26. The method according to claim 24, wherein the alkylating agent is a compound of the formula $R^4Y$;

wherein $R^4$— is $R^5OCH_2$—, $R^5OCH_2CH_2OCH_2$—, $R^5SCH_2$—, $(R^5)_3SiCH_2CH_2OCH_2$—, $HOCH_2CH_2$—, $R^5OC(O)$—, $R^5OC(S)$—, $(R^5)(R^5)NC(O)$—, $(R^5)(R^5)(R^5)Si$—, $(R^5)(R^5)(R^5)Sn$—, $(R^5)(R^5)S(O)_2CH_2$—, $(R^5)(R^5)S(O)_2CH(R^5)$— and $(R^5)(R^5)S(O)_2C(R^5)(R^5)$—;

—Y is fluoro, chloro, bromo, iodo, —$OSO_2CH_3$, —$OSO_2CF_3$—, —$OSO_2C_6H_4$-p-$CH_3$, —$OSO_2C_6H_4$-p-Br, —CN, —O($C_1$–$C_6$ alkyl) and —OC(O) ($C_1$–$C_6$ alkyl); and each $R^5$ is independently $C_1$–$C_6$ straight or branched chain alkyl, $C_3$–$C_6$ cycloalkyl, ($C_1$–$C_6$ straight or branched chain alkyl)$_3$Si($C_1$–$C_6$ straight or branched chain alkyl), ($C_3$–$C_6$ cycloalkyl)$_3$Si($C_1$–$C_6$ straight or branched chain alkyl), $C_1$–$C_6$ straight or branched chain alkyl-C(O)— or, when $R^5$ is bonded to a nitrogen atom, $C_1$–$C_6$ straight or branched chain alkyl-OC(O)—.

27. The method according to claim 26, wherein the leaving group in the 2-position of the 3-N-alkylated 1-(4-fluorophenylmethyl)-1H-benzimidazolium salt is the same as —Y.

28. The method according to claim 24, wherein the protecting group is a sulfonyl group, an acid labile alkyl group, an acyl or alkoxycarbonyl group.

29. The method according to claim 28, wherein the alkyoxycarbonyl group is an ethoxycarbonyl group, and the acyl group is an acetyl or a trimethylacetyl group.

30. The method according to claim 24, wherein the step of reacting the 2-(4-amino-1-N-protected piperidinyl)-substituted 3-N-alkylated 1-(4-fluorophenylmethyl)-1H-benzimidazolium salt with the hydrolytic or nucleophilic agent comprises:

(i) reacting the 2-(4-amino-1-N-protected piperidinyl)-substituted 3-N-alkylated 1-(4-fluorophenylmethyl)-1H-benzimidazolium salt with a boron trihalide to afford a dealkylation product; and (ii) reacting the dealkylation product with a mineral acid to afford protected norastemizole.

31. The method according to claim 24, wherein the step of hydrolyzing comprises reacting the protected norastemizole with an aqueous base having a pH of about 9 to about 14, or with concentrated mineral acid having a pH of about 0–1.

32. A method of preparing norastemizole which comprises:

(a) alkylating a 2-halosubstituted 1-(4-fluorophenylmethyl)-1H-benzimidazole to yield a 3-N-alkylated 2-halosubstituted 1-(4-fluorophenylmethyl)-1H-benzimidazolium salt;

(b) reacting said salt with a 1-N-substituted 4-aminopiperidine to form an adduct; and (c) hydrolyzing said adduct to form norastemizole.

33. The method of claim 8, wherein the nucleophile is a 1-N-protected 4-aminopiperidine.

34. A method for synthesizing a 2-substituted imidazole, which comprises reacting a displacement nucleophile, in the presence of fluoride ion, with an imidazole of formula I

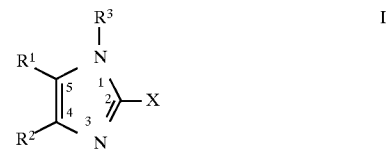

wherein $R^1$, $R^2$ and $R^3$ are independently hydrogen, $C_1$–$C_{12}$ branched or straight chain alkyl, $C_3$–$C_8$ cycloalkyl, phenyl, naphthyl and benzyl, said $C_1$–$C_{12}$ branched or straight chain alkyl, $C_3$–$C_8$ cycloalkyl, phenyl, naphthyl and benzyl groups being optionally substituted with one or more halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), carboxyl, phenyl, —C(O)O—$C_1$–$C_6$ alkyl or —C(O)$C_1$–$C_6$ alkyl groups, except that $R^3$ is not —C(O)$C_1$–$C_6$ alkyl; or either $R^1$ and $R^2$, or $R^1$ and $R^3$, is joined to form a $C_3$–$C_8$ saturated or unsaturated cycloalkyl group, aromatic group, or heteroaromatic group, said $C_3$–$C_8$ saturated or unsaturated cycloalkyl group, aromatic group, or heteroaromatic group being optionally substituted with one or more members of the group consisting of halogen, hydroxyl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), —S(O)$_2$($C_1$–$C_6$ alkyl), carboxyl, phenyl and —C(O)O—$C_1$–$C_6$ alkyl; or $R^1$ and $R^2$ are independently —NHC(O) ($C_1$–$C_6$ alkyl), —N($C_1$–$C_6$ alkyl)C(O) ($C_1$–$C_6$ alkyl), —C(O)NH ($C_1$–$C_6$ alkyl) or —C(O)N($C_1$–$C_6$ alkyl) ($C_1$–$C_6$ alkyl); and X is selected from the group consisting of fluoro, chloro, bromo, iodo, —$OSO_2CH_3$, —$OSO_2CF_3$, —$OSO_2C_6H_4$-p-$CH_3$, —$OSO_2C_6H_4$-p-Br, —OC(O) ($C_1$–$C_6$ alkyl), —$N^+$($C_1$–$C_6$ alkyl) ($C_1$–$C_6$ alkyl) ($C_1$–$C_6$ alkyl) and —$S^+$($C_1$–$C_6$ alkyl) ($C_1$–$C_6$ alkyl); and wherein the nucleophile (1) displaces said leaving group from the 2-position of the imidazole and (2) forms a bond with the 2-carbon atom thereof.

35. The method according to claim 34, wherein the $C_3$–$C_8$ saturated or unsaturated cycloalkyl group, is selected from the group consisting of a substituted or unsubstituted cyclopropane, cyclobutane, cyclobutene, methylcyclobutane, cyclopentane, cyclopentene, cyclohexane, cyclohexene, methylcyclohexane and dimethylcyclohexane.

36. The method according to claim 34, wherein the aromatic group is selected from the group consisting of a substituted or unsubstituted benzene group, toluene group, and xylene group.

37. The method according to claim 34, wherein the heteroaromatic group is selected from the group consisting of thienyl, furyl, 2H-pyrrolyl, imidazolyl, pyrazolyl, pyridyl, pyrazinyl, pyrimidinyl and pyridazinyl.

38. The method according to claim 34, wherein the nucleophile is $NH_3$, $NH_2$($C_1$–$C_6$ alkyl), $NH_2$($C_3$–$C_8$ cycloalkyl), $NH_2$(phenyl), $NH_2$(Het), $NH(C_1$–$C_6$ alkyl) ($C_1$–$C_6$ alkyl), NH(phenyl) ($C_1$–$C_6$ alkyl), NH(Het) ($C_1$–$C_6$ alkyl), NH(phenyl) (phenyl), NH(phenyl) (Het), NH(Het) (Het), $NH_2NH_2$, $MN_3$, HO($C_1$–$C_6$ alkyl), HO($C_1$–$C_6$ alkenyl), HO($C_1$–$C_6$ alkynyl), HO($C_3$–$C_8$ cycloalkyl), HO($C_3$–$C_8$ cycloalkenyl), HS($C_1$–$C_6$ alkyl), HS($C_1$–$C_6$ alkenyl), HS($C_1$–$C_6$ alkynyl), HS($C_3$–$C_8$ cycloalkyl), HS($C_3$–$C_8$ cycloalkenyl), HO-phenyl, HO-naphthyl, MSi ($C_1$–$C_6$ alkyl) ($C_1$–$C_6$ alkyl) ($C_1$–$C_6$ alkyl), ($C_1$–$C_6$ alkyl) Mg(halogen), ($C_1$–$C_6$ alkenyl)Mg(halogen), ($C_1$–$C_6$ alkyl) Li, ($C_1$–$C_6$ alkenyl)Li, ($C_1$–$C_6$ alkyl)$_2$Zn, ($C_1$–$C_6$ alkenyl) $_2$Zn, ($C_1$–$C_6$ alkyl)CeCl$_2$, MZn($C_1$–$C_6$ alkyl) ($C_1$–$C_6$ alkyl) ($C_1$–$C_6$ alkyl), Br$^-$, I$^-$, MP($C_1$–$C_6$ alkyl)$_2$, HP($C_1$–$C_6$ alkyl) $_2$, H$_2$N($C_1$–$C_6$ alkyl), H$_2$N($C_1$–$C_6$ alkenyl) and H$_2$N($C_1$–$C_6$ alkynyl), wherein M is Na$^+$ Li$^+$, K$^+$ $^+$Mg(halogen), $^+$Mn(halogen), $^+$Zn(halogen), $^+$Sn(halogen), each Het is independently 2-pyrrolyl, 3-pyrrolyl, 2-imidazolyl, 4-imidazolyl, 5-imidazolyl, 3-pyrazolyl, 4-pyrazolyl, 5-pyrazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 3-isoxazolyl, 4-isoxazolyl, 5-isoxazolyl, 3-isothiazolyl, 4-isothiazolyl, 5-isothiazolyl, 2-imidazolidinyl, 4-imidazolidinyl, 3-pyrazolidinyl, 4-pyrazolidinyl, 2-piperidinyl, 3-piperidinyl, 4-piperidinyl, 2-piperazinyl, 3-piperazinyl, 4-piperazinyl, 2-morpholinyl or 3-morpholinyl, and the nucleophile being optionally substituted, at either a carbon atom or a heteroatom, with one or more halogen, hydroxyl, sulfhydryl, nitro, cyano, trifluoromethyl, $C_1$–$C_6$ alkyl, $C_1$–$C_6$ alkoxyl, $C_1$–$C_6$ alkylthio, —N($C_1$–$C_6$ alkyl) ($C_1$–$C_6$ alkyl), carboxyl, phenyl, $C_1$–$C_6$ alkoxylcarbonyl and ($C_1$–$C_6$ alkyl)-CO groups.

39. The method according to claim 34, wherein the nucleophile has more than one nucleophilic group, and one of the nucleophilic groups of the nucleophile is protected with a protecting group.

40. The method according to claim 39, wherein the protecting group is a sulfonyl group, an acid labile alkyl group, an acyl or alkoxycarbonyl group.

41. The method according to claim 34, wherein the fluoride ion is in the form of a fluoride salt.

42. The method according to claim 41, wherein the fluoride salt is selected from the group consisting of TBAF, TBAF.XH$_2$O, CsF, RbF, NaF, LiF, KF, KF/CaF$_2$ and mixtures thereof.

43. The method of claim 34, wherein the method is performed in the presence of a phase transfer catalyst.

44. The method of claim 43, wherein the phase transfer catalyst is trioctylmethylammonium chloride.

45. A method for the synthesis of norastemizole, which comprises:

(a) reacting, in the presence of fluoride ion, a 1-(4-fluorophenylmethyl)-1H-benzimidazole having a leaving group in the 2-position, with a 1-N-protected 4-aminopiperidine which (1) displaces said leaving group from the 2-position of the 1-(4-fluorophenylmethyl)-1H-benzimidazole and (2) forms a bond with the 2-carbon atom thereof to afford norastemizole having a protecting group on the nitrogen atom of the piperidine moiety thereof; and (b) hydrolyzing the norastemizole having a protecting group on the nitrogen atom of the piperidine moiety thereof to afford norastemizole.

46. The method according to claim 45, wherein the fluoride ion is in the form of a fluoride salt.

47. The method according to claim 45, wherein the fluoride salt is selected from the group consisting of TBAF, TABAF.XH$_2$O, CsF, RbF, NaF, LiF, KF, KF/CaF$_2$ and mixtures thereof.

48. The method according to claim 45, wherein the leaving group is selected from the group consisting of fluoro, chloro, bromo, iodo, —OSO$_2$CH$_3$, —OSO$_2$CF$_3$, —OSO$_2$C$_6$H$_4$-p-CH$_3$, —OSO$_2$C$_6$H$_4$-p-Br, —OC(O) ($C_1$–$C_6$ alkyl), —N$^+$($C_1$–$C_6$ alkyl) ($C_1$–$C_6$ alkyl) ($C_1$–$C_6$ alkyl) and —S$^+$($C_1$–$C_6$ alkyl) ($C_1$–$C_6$ alkyl).

49. The method according to claim 45, wherein the N-protected 4-aminopiperidine is an acyl or alkoxycarbonyl protected 4-aminopiperidine.

50. The method according to claim 49, wherein the acyl protected 4-aminopiperidine is 4-N-acetylaminopiperidine or 4-N-trimethylacetylaminopiperidine.

51. The method according to claim 49, wherein the alkoxycarbonyl protected 4-aminopiperidine is ethyl 4-amino-1-piperidine carboxylate.

52. The method according to claim 45, wherein the step of hydrolyzing the norastemizole having a protecting group on the nitrogen atom of the piperidine moiety thereof comprises acid hydrolysis.

53. The method according to claim 45, wherein the step of hydrolyzing the norastemizole having a protecting group on the nitrogen atom of the piperidine moiety thereof comprises base hydrolysis.

54. The method according to claim 45, wherein the method is performed in the additional presence of a phase transfer catalyst.

55. The method according to claim 54, wherein the phase transfer catalyst is trioctylmethylammonium chloride.

56. The method according to claim 42, wherein the imidazole of formula I is in an amount of 1 molar equivalent, and the fluoride salt is in an amount that ranges from catalytic to about 5 molar equivalents.

57. The method according to claim 47, wherein the 1-(4-fluorophenylmethyl)-1H-benzimidazole is in an amount of 1 molar equivalent, and the fluoride salt is in an amount that ranges from catalytic to about 5 molar equivalents.

* * * * *